United States Patent
Hebel et al.

(10) Patent No.: US 7,238,522 B2
(45) Date of Patent: Jul. 3, 2007

(54) DEVICES AND METHODS FOR BIOMATERIAL PRODUCTION

(75) Inventors: Henry Hebel, The Woodlands, TX (US); Sriram Ramakrishnan, The Woodlands, TX (US); Hugo Gonzalez, Houston, TX (US); Jeff Darnell, The Woodlands, TX (US)

(73) Assignee: ADViSYS, Inc., The Woodlands, TX (US)

(*) Notice: Subject to any disclaimer, the term of this patent is extended or adjusted under 35 U.S.C. 154(b) by 0 days.

(21) Appl. No.: 10/857,439

(22) Filed: May 27, 2004

(65) Prior Publication Data
US 2005/0014245 A1   Jan. 20, 2005

Related U.S. Application Data

(60) Provisional application No. 60/474,749, filed on May 30, 2003.

(51) Int. Cl.
*C12M 1/33* (2006.01)
(52) U.S. Cl. .............. 435/306.1; 435/297.2; 435/259; 241/2; 366/101; 366/279
(58) Field of Classification Search ............. 435/259, 435/306.1, 289.1, 813; 241/2; 366/101, 366/107
See application file for complete search history.

(56) References Cited

U.S. PATENT DOCUMENTS

| | | | |
|---|---|---|---|
| 4,533,123 A | 8/1985 | O'Leary et al. |
| 5,438,128 A | 8/1995 | Nieuwkerk et al. |
| 5,482,836 A | 1/1996 | Cantor et al. |
| 5,561,064 A | 10/1996 | Marquet et al. |
| 5,591,841 A | 1/1997 | Ji et al. |
| 5,625,053 A | 4/1997 | Kresheck et al. |
| 5,650,506 A | 7/1997 | Woodard et al. |
| 5,665,554 A | 9/1997 | Reeve et al. |
| 5,693,785 A | 12/1997 | Woodard et al. |

(Continued)

FOREIGN PATENT DOCUMENTS

EP   0 967 269   12/1999

(Continued)

OTHER PUBLICATIONS

Birnboim and Doly, 1979, *Nucleic Acids Res.* 7, 1513-1523.

(Continued)

*Primary Examiner*—William H. Beisner
(74) *Attorney, Agent, or Firm*—Jackson Walker L.L.P.

(57) ABSTRACT

An apparatus and a method for isolating a biologic product, such as plasmid DNA, from cells. The method involves lysing cells in a controlled manner separate insoluble components from a fluid lysate containing cellular components of interest, followed by membrane chromatographic techniques to purify the cellular components of interest. The process utilizes a unique lysis apparatus, ion exchange and, optionally, hydrophobic interaction chromatography membranes in cartridge form, and ultrafiltration. The process can be applied to any biologic product extracted from a cellular source. The process uses a lysis apparatus, including a high shear, low residence-time mixer for advantageously mixing a cell suspension with a lysis solution, a hold time that denatures impurities, and an air-sparging bubble mixer that gently yet thoroughly mixes lysed cells with a neutralization/precipitation buffer and floats compacted precipitated cellular material.

14 Claims, 5 Drawing Sheets

U.S. PATENT DOCUMENTS

| | | | |
|---|---|---|---|
| 5,707,812 A | 1/1998 | Horn et al. | |
| 5,808,041 A | 9/1998 | Padhye et al. | |
| 5,837,529 A | 11/1998 | Wan et al. | |
| 5,843,731 A | 12/1998 | Yamamoto et al. | |
| 5,898,071 A | 4/1999 | Hawkins et al. | |
| 5,981,735 A | 11/1999 | Thatcher et al. | |
| 5,986,085 A | 11/1999 | Gjerde et al. | |
| 5,990,301 A | 11/1999 | Colpan et al. | |
| 6,011,148 A | 1/2000 | Bussey et al. | |
| 6,197,553 B1 | 3/2001 | Lee et al. | |
| 6,235,892 B1 | 5/2001 | Demmer et al. | |
| 6,395,516 B1 | 5/2002 | Nienow et al. | |
| 6,410,274 B1 | 6/2002 | Bhikhabhai et al. | |
| 2001/0034435 A1 | 10/2001 | Nochumson et al. | |
| 2002/0198372 A1 | 12/2002 | Bridenbaugh et al. | |

FOREIGN PATENT DOCUMENTS

| | | | |
|---|---|---|---|
| WO | WO 97/35002 | 9/1997 | |
| WO | WO 98/30685 | 7/1998 | |
| WO | WO 00/05 358 | 2/2000 | |
| WO | WO 00/05358 | 2/2000 | |
| WO | WO 00/53304 | 9/2000 | |
| WO | WO 01/94 573 | 12/2001 | |
| WO | WO 01/94573 | 12/2001 | |
| WO | WO 2004/024283 | 3/2004 | |

OTHER PUBLICATIONS

Carlson et al., 1995, *Biotechnol. Bioeng.* 48, 303-315.

Levy et al., 2000, *Trends Biotechnol.* 18, 296-305.

Marquet et al., 1995, *Biopharm* 8, 26-37.

Rathore et al., 2003, *Biopharm International*, March, 30-40.

Varley et al., 1999, *Bioseparation* 8, 209-217.

Ferreira et al., titled "*Downstream Processing of Plasimid DNA for Gene Therapy and DNA Vaccine Applications*," Trends in Biotechnology, Elsevier, vol. 18 p. 380-388 (Sep. 2000).

DEVICES AND METHODS FOR BIOMATERIAL PRODUCTION

RELATED APPLICATIONS

This application claims priority to U.S. Provisional Patent Application Ser. No. 60/474,749, entitled "Devices and Methods for Biomaterial Production," filed on May 30, 2003, having Hebel et al., listed as inventors, the entire content of which is hereby incorporated by reference.

BACKGROUND

The present invention relates to an apparatus and scalable methods of lysing cells. The invention also relates to methods of isolating and purifying cellular components from lysed cells. The invention is particularly suited for scalable lysis of plasmid-containing bacterial cells, and subsequent preparation of large quantities of substantially purified plasmid. The resulting plasmid is suitable for a variety of uses, including but not limited to gene therapy, plasmid-mediated hormonal supplementation or other therapy, DNA vaccines, or any other application requiring substantial quantities of purified plasmid. Over the last five years, there has been an increased interest in the field of plasmid processing. The emergence of the non-viral field has caused researchers to focus on a variety of different methods of producing plasmids.

Because plasmids are large and complex macromolecules, it is not practical to produce them in large quantities through synthetic means. Instead, they must be initially produced in biological systems, and subsequently isolated and purified from those systems. In virtually all cases, biological production of plasmids takes the form of fermenting *Escherichia coli* (*E. coli*) cells containing the plasmid of interest. A number of techniques for fermenting plasmid-containing *E. coli* cells have been known by those skilled in the art for many years. Many fermentation processes have been published, are well known and are available in the public domain.

Cell lysis and the subsequent treatment steps used to prepare a process stream for purification are the most difficult, complex and important steps in any plasmid process. It is in this process step where yield and quality of the plasmid of interest are primarily determined for each run. The search for an optimal method, one that is continuous and truly scalable, has been an obstacle in getting acceptable processes with commercial applicability.

There are a variety of ways to lyse bacterial cells. Well-known methods used at laboratory scale for plasmid purification include enzymatic digestion (e.g. with lysozyme), heat treatment, pressure treatment, mechanical grinding, sonication, treatment with chaotropes (e.g. guanidinium isothiocyante), and treatment with organic solvents (e.g. phenol). Although these methods can be readily practiced at small scale, few have been successfully adapted for large-scale use in preparing plasmids.

Methods such as pressure treatment, mechanical grinding, or sonication can be difficult to implement at large scale. Moreover, Carlson et al. (1995, *Biotechnol. Bioeng.* 48, 303–315) have shown that such mechanical methods can lead to unacceptable plasmid degradation. Methods involving chaotropes and/or organic solvents are problematic to scale up because these chemicals are typically toxic, flammable, and/or explosive. Handling and disposing of such chemicals is manageable at small scale, but generally creates substantial problems at large scale. U.S. Pat. No. 6,197,553 describes a large-scale lysis technique involving treatment with lysozyme and heat. However, this technique requires carefully controlled heating and cooling of the enzymatically-treated bacterial cells to achieve lysis. The technique also has disadvantages in that it requires the use of an animal-derived enzyme (lysozyme), which can be expensive and is a potential source of biological contamination. Using animal-derived materials is quickly becoming unacceptable when preparing plasmids or other cellular components of interest for human or veterinary applications.

Currently, the preferred method for lysing bacteria for plasmid purification is through the use of alkali and detergent. This technique was originally described by Birnboim and Doly (1979, *Nucleic Acids Res.* 7, 1513–1523). A commonly used variation of this procedure, as described on pp. 1.38–1.39 of Sambrook et al. (*Molecular Cloning: A Laboratory Manual*, $2^{nd}$ Ed., Cold Spring Harbor Laboratory Press, Cold Spring Harbor, N.Y.), is to suspend bacterial cells in 10 mL of a resuspension solution, consisting of 50 mM glucose, 25 mM Tris, pH 8.0, 10 mM EDTA. The suspension is mixed with 20 mL of a lysis solution, consisting of 0.2 N NaOH, 1% sodium dodecylsulfate (SDS) and incubated for 5–10 minutes. During this period, the cells lyse and the solution becomes highly viscous. The high pH denatures both the host genomic DNA and the plasmid DNA. The SDS forms complexes with cellular proteins, lipids, and membrane components, some of which are tightly associated with the host genomic DNA. The lysate-mixture is next treated with 15 mL of an ice-cold neutralization/precipitation solution, consisting of 3 M potassium acetate that has been adjusted to pH 5.5 with acetic acid. This acidified mixture is incubated on ice for 5–10 minutes, in part to allow plasmid DNA to renature. During this time, a white flocculent precipitate is formed. The precipitate comprises potassium SDS, which is poorly soluble under these conditions. In addition, the precipitate contains host genomic DNA, proteins, lipids, and membrane components, which remain bound to the SDS. The precipitate is subsequently removed by filtration or centrifugation, yielding a clarified lysate containing the desired plasmid, which can be subjected to various purification procedures.

This lysis method has very distinct advantages over those described above. In addition to providing efficient release of plasmid molecules from the cells, this procedure provides substantial purification of the plasmid by removing much of the host protein, lipids, and genomic DNA. Removal of genomic DNA is particularly valuable, since it can be difficult to separate it from plasmid DNA by other means. These advantages have made this a preferred method for lysing bacterial cells during plasmid purification at laboratory scale.

Unfortunately, this method presents significant challenges for scaling up. First, thorough mixing of suspended cells with lysis solution is easily managed at small scale by simply vortexing or repeatedly inverting the vessel containing the cells. However, this is impractical at large scale, where volumes may be in the range of tens or hundreds of liters. Common techniques for mixing large volumes of liquid, such as batch impeller mixing, are problematic because as some cells begin to lyse after initial mixing, they release genomic DNA that dramatically increases solution viscosity. This increase in viscosity significantly interferes with further mixing.

A second challenge is that excessive incubation at high pH after addition of alkaline lysis solution can lead to permanent denaturation of the plasmid, making it unsuitable for most subsequent uses. It is therefore necessary to ensure that the lysed cells are thoroughly mixed with neutralization/precipitation solution within a relatively narrow time frame, typically within 5–10 minutes. It is also well known that mixing at this step must be gentle (i.e. low shear). Vigorous (i.e. high shear) mixing at this step releases substantial amounts of material from the flocculent precipitate into the plasmid-containing solution. This includes large amounts of host genomic DNA and endotoxins. These substances are difficult to separate from the plasmid during subsequent purification. Thus, while complete mixing is required to precipitate all of the SDS-associated impurities and renature all of the plasmid, mixing should also be as gentle as possible. This is easily accomplished at small scale by timed addition of neutralization/precipitation solution using hand mixing techniques such as gentle swirling or inversion of the containers. In contrast, rapid yet gentle mixing is difficult to achieve at large scale. Low shear stirring or impeller mixing in batch mode requires relatively long times to achieve complete mixing, which could result in unacceptably high levels of permanently denatured plasmid. More rapid techniques such as high speed impeller mixing are likely to result in unacceptably high levels of genomic DNA and endotoxin in the plasmid-containing solution.

It has previously been believed that mixing a cell suspension and a lysis solution must be performed at very low shear. This has been particularly claimed in regard to mixing suspensions of plasmid-containing bacteria with lysis solutions comprising alkali and detergent. For example, Wan et al., in U.S. Pat. No. 5,837,529, in discussing methods of lysing plasmid-containing cells with alkali or enzymes, contend that it is crucial to handle such lysates very gently to avoid shearing genomic DNA. Similarly, Nienow et al., in U.S. Pat. No. 6,395,516, in discussing the challenges of alkaline lysis, claim that too vigorous mixing at any stage of the procedure may lead to fragmentation of genomic DNA, which may substantially contaminate the final purified product. Yet again, Bridenbaugh et al., in U.S. Patent Application No. 2002/0198372, emphasize the need for gentle mixing of cells with lysis solution. These concerns have led such investigators to develop ostensibly scalable means to gently mix suspended cells with lysis solutions. For instance, U.S. Pat. No. 5,837,529 and U.S. Patent Application No. 2002/0198372 each contemplate using static mixers to achieve continuous low shear mixing, while U.S. patent application Ser. No. 6,395,516 contemplates using a designed vessel for controlled mixing in batch mode. Such methods have clear drawbacks. In one regard, while striving to minimize excessive shear, mixing of the cell suspension with the lysis solution may be incomplete. In another regard, using static mixers limits process flexibility. As described in U.S. Patent No. 2002/0198372, it is necessary to optimize the number of static mixing elements, as well as the flow rates of the fluids passing through the elements. Such optimization restricts the amount of material that may be processed in a given time with the optimized static mixing apparatus. This limits the ability to increase process scale, unless a new, higher-capacity static mixing apparatus is constructed and optimized. Use of batch mixing vessels, as described in U.S. Pat. No. 6,395,516, has comparable drawbacks. Achieving complete mixing in all regions of a batch mixing vessel is well known by those of skill in the art to be challenging. Furthermore, batch mixing vessels are poorly suited for applications that require a controlled exposure time wherein the cell suspension is contacted with the lysis solution. In particular, it is well known that prolonged exposure of plasmid-containing cells to alkali may lead to the formation of excessive amounts of permanently denatured plasmid, which is generally inactive, undesirable, and difficult to subsequently separate from biologically active plasmid. Typically, it is desirable to limit such exposure times to about 10 minutes or less. Achieving such limited exposure times is difficult or impossible using large scale batch mixing.

Removal of the flocculent precipitate is yet another challenge in scaling up alkaline lysis. Complete removal is desirable to eliminate the genomic DNA and other impurities trapped in the precipitate. At the same time, the precipitate must not be subjected to excessive shear. Otherwise, large amounts of genomic DNA, endotoxins, and other impurities are released from the precipitate and contaminate the plasmid-containing solution. At laboratory scale, the precipitate is readily removed by simple filtration, batch centrifugation, or both. However, batch centrifugation is highly impractical at large scale. Continuous centrifugation at large scale is also unsuitable because it subjects the precipitate to high shear stress, releasing unacceptable levels of impurities. Filtration at large scale is problematic due to the somewhat gelatinous, cheese-like consistency of the precipitate, which readily clogs even depth or bag filters.

Notwithstanding the above challenges, a variety of investigators have developed claimed improvements of the alkaline lysis method, or otherwise attempted to adapt it into a scalable production process. Kresheck and Altschuler, in U.S. Pat. No. 5,625,053, describe the use of non-ionic alkyldimethylphosphine oxide detergents in place of SDS. Use of these detergents is claimed to offer certain advantages relevant to large-scale preparation of pharmaceutical grade plasmid. However, the claimed improvements do not address the scalability issues described above.

Thatcher et al., in U.S. Pat. No. 5,981,735, describe a modification where the amount of NaOH added to the suspended cells is carefully controlled to ensure that the pH remains approximately 0.1 pH units below the point that results in substantial permanent denaturation of plasmid. This approach may address the issue of time-dependent generation of permanently denatured plasmid, but requires very precise pH control, which can be difficult at large scale. Furthermore, the preferred pH level must be determined in advance for each plasmid and host cell combination. Most importantly, this approach does not address the challenges of handling and mixing large liquid volumes.

Wan et al., in U.S. Pat. No. 5,837,529, describe a process of lysing cells, comprising the use of static mixers to mix suspended cells with a lysis solution (e.g. 0.2 N NaOH, 1% SDS), as well as to mix lysed cells with a precipitating solution (e.g. 3 M potassium acetate, pH 5.5). Static mixers are claimed to be particularly advantageous by providing a high degree of mixing at a relatively low shear, and are also amenable to a continuous flow-through process. A similar process using static mixers is described by Bridenbaugh et al. in WO 00/05358. Such procedures offer certain advantages, but drawbacks remain. As shown in WO 00/05358, both the number of static mixing elements and the solution linear flow rates must be carefully controlled at each stage. Using too few mixing elements or a low linear flow rate leads to inadequate mixing and poor plasmid yields. Using too many elements or a high linear flow rate leads to excessive shearing and release of genomic DNA into solution. These parameters must be experimentally optimized, and any efforts to increase process scale require re-optimization of element number and flow rate, limiting process flexibility and the robustness of this method for routine use.

Marquet et al. (1995, *Biopharm* 8, 26–37) describe the use of batch mixers originally designed for use in the food industry. They claim that these mixers can provide thorough mixing at low shear rates, making them suitable for use during large-scale alkaline lysis of plasmid-containing cells. However, batch mixing of large fluid volumes in tanks is often very difficult to scale up, particularly when there are dramatic differences in fluid viscosity, or when mixing itself leads to dramatic increases in viscosity. Batch mixing is also problematic when coupled with short, time-sensitive incubation steps. All of these concerns pertain to alkaline lysis, making batch mixing particularly unsuitable.

Thus, despite the efforts of previous investigators, there is still a clear need for new and improved procedures to perform alkaline lysis at large scale. A preferred process would address a series of key challenges, including: (1) thorough, rapid, and robust mixing of cells and lysis solution, to efficiently lyse cells and release plasmid; (2) time-controlled incubation of lysed cells in alkali, to prevent permanent plasmid denaturation; (3) thorough, rapid, and gentle mixing of alkaline lysate with neutralization/precipitation solution, to efficiently precipitate contaminating cellular components without releasing excess genomic DNA and endotoxin into the plasmid-containing solution; and (4) efficient yet gentle removal of the flocculent precipitate, again without releasing excess genomic DNA and endotoxin into the plasmid-containing solution. Furthermore, such a preferred process would be readily scalable, robust, suitable for use in all applications, would contain no animal derived products, and would be cost effective.

There is also a need for improved procedures for purifying plasmids from large-scale microbial cell lysates. In particular, the emerging fields of non-viral gene therapy, plasmid-mediated therapy and DNA vaccines require gram or even kilogram amounts of purified plasmid suitable for pharmaceutical use. It is thus necessary to purify plasmids away from the primary impurities remaining in the lysate, including residual genomic DNA, RNA, protein, and endotoxin. An ideal process should provide substantially pure material in high yield, be easy to scale up, involve a minimal number of steps, and be simple and inexpensive to perform. Any use of enzymes or animal-derived products should be avoided, as such reagents tend to be expensive and more importantly, are potential sources of contamination. Similarly, use of alcohols and organic solvents is to be avoided, as they are generally toxic, flammable, explosive, and difficult to dispose of in large quantities. Known or suspected toxic, mutagenic, carcinogenic, teratogenic, or otherwise harmful compounds should not be used. Finally, the process should avoid the need for expensive equipment such as large scale or continuous centrifuges, or gradient producing chromatography skids.

Various attempts have been made to develop a plasmid purification process that meets these ideals. For example, Horn et al., in U.S. Pat. No. 5,707,812, describe an integrated process involving alkaline lysis, filtration with diatomaceous earth, concentration and desalting by ultrafiltration/diafiltration (UF/DF), overnight precipitation of plasmid with 8% polyethylene glycol (PEG) 8000, centrifugation, resuspension, precipitation of impurities with 2.5 M ammonium acetate, centrifugation, precipitation of plasmid with isopropanol, centrifugation, resuspension, anion exchange column chromatography in the presence of 1% PEG 8000 on Q Sepharose™ (Amersham Biosciences Corp., Piscataway, N.J.) with step elution, plasmid precipitation with isopropanol, centrifugation, resuspension, and gel filtration column chromatography on Sephacryl™ S-1000 (Amersham Biosciences Corp., Piscataway, N.J.). Plasmid yields, quality, and purity were not described.

Similar processes are disclosed by Marquet et al. in U.S. Pat. No. 5,561,064. These processes are not easily scaled, due to the multiple plasmid precipitations and centrifugations. In addition, achieving adequate resolution with gel filtration column chromatography typically requires relatively large columns. Use of isopropanol in multiple steps is another disadvantage of this process.

U.S. Pat. No. 5,990,301, issued to Colpan et al., describes an integrated process involving alkaline lysis, clarification by centrifugation and filtration, incubation with salt (NaCl) and nonionic detergent, anion exchange by DEAE column chromatography, isopropanol precipitation, centrifugation, and resuspension. The resulting plasmid was reported to contain "no detectable" RNA, genomic DNA, or endotoxin, but detection methods and limits were not described. This process has numerous scalability issues. DEAE resins typically have relatively low capacity for plasmid. Furthermore, using isopropanol precipitation and centrifugation for product concentration and desalting is not feasible at large scale.

U.S. Pat. No. 6,197,553, issued to Lee and Sagar, describes an integrated process involving cell wall digestion with lysozyme, lysis by passing through a flow-through heat exchanger to heat the cell suspension to about 80° C., clarification by centrifugation, diafiltration, treatment with RNase, diafiltration, anion exchange column chromatography on POROS® PI/M (Applied Biosystems, Foster City, Calif.) with NaCl gradient elution, reverse phase chromatography on POROS® R2/M with isopropanol gradient elution, and UF/DF. Final product contained 2.9% genomic DNA, <1% protein, <1% RNA, and endotoxin levels of 2.8 endotoxin units (EU) per milligram of plasmid. However, this process suffers from the use of two enzymes (lysozyme and RNase), gradient-based anion exchange chromatography, and gradient-based reverse phase chromatography using isopropanol. These present substantial scalability and/or regulatory issues.

U.S. Pat. No. 6,410,274, issued to Bhikhabhai, describes a process involving alkaline lysis, filtration, precipitation of RNA and genomic DNA with $CaCl_2$, centrifugation, filtration, anion exchange column chromatography on Q Sepharose™ XL (Amersham Biosciences Corp., Piscataway, N.J.) with step elution, and further anion exchange column chromatography on Source™ 15Q (Amersham Biosciences Corp., Piscataway, N.J.) with step elution. Final product was reported to contain 0.6% genomic DNA (by PCR), 100% supercoiled plasmid (by anion exchange high performance liquid chromatography, "HPLC"), and no detectable RNA (by reverse phase HPLC), protein (by Micro BCA™ assay, Pierce Biotechnology, Rockford, Ill.), or endotoxin (by *limulus amebocyte* lysate, "LAL"). The use of two successive anion exchange steps is an obvious inefficiency of this process. Furthermore, the process relies on column chromatographic techniques, which involve expensive hardware and resins.

WO 00/05358, submitted by Bridenbaugh et al., describes a process where plasmid-containing cells are resuspended in the presence of RNase. A continuous lysis procedure is described, where the resuspended cells and an alkaline lysis solution are simultaneously pumped through a static mixer to achieve lysis. The lysate is then mixed with potassium acetate precipitation solution via a second static mixer. The precipitated lysate then passes into a continuous centrifuge to remove the flocculent precipitate, resulting in a clarified lysate. Clarified lysate is filtered to remove fine particulates and purified by anion exchange column chromatography using Fractogel® TMAE-650M (Merck KGaA, Darmstadt, Germany). The anion exchange eluate is then passed through glass and nylon filters, which are claimed to help remove endotoxin and genomic DNA. Purified plasmid was then concentrated and desalted by UF/DF, and sterilized by filtration. Final endotoxin levels were 16.2 EU/mg. Residual RNA, protein, and genomic DNA were said to routinely be <2%, <0.1%, and <1%, respectively. Use of continuous centrifugation is a significant drawback of this process, due to high shear rates and subsequent release of excess genomic DNA into solution, as well as the high cost of such equipment. Use of RNase is a further drawback of this process from a regulatory standpoint.

U.S. Patent Application No. 2001/0034435, submitted by Nochumson et al., describes a process where plasmid-containing cells are lysed with alkali and SDS in a continuous process using static mixers. The lysate is neutralized by continuous addition (via a second set of static mixers) of a neutralization/precipitation solution. The neutralized lysate is held for 6–12 hours at 4° C. to precipitate the majority of the RNA. The flocculent precipitate and the precipitated RNA are removed by centrifugation and/or filtration, and the plasmid-containing solution is subjected to anion exchange column chromatography using Fractogel® TMAE-650S (Merck KGaA, Darmstadt, Germany). Plasmid is then eluted and subjected to hydrophobic interaction chromatography ("HIC"), also in column format, using Octyl Sepharose™ 4FF (Amersham Biosciences Corp., Piscataway, N.J.). Under appropriate conditions, genomic DNA, RNA, and endotoxin bind to the resin, while plasmid passes through. After HIC, the product is concentrated and desalted by UF/DF, and sterile filtered. Detailed information on yields and purity were not described in this application. However, plasmid binding capacities for the resins are relatively low (1–3 mg/mL for the anion exchange, and <1 mg/mL for the HIC if used in binding mode), and again, there is a reliance on column chromatography.

Varley et al. (1999, Bioseparation 8, 209–217) describe a process consisting of optimized alkaline lysis with RNase treatment, bag depth filtration, expanded bed anion exchange chromatography, ultrafiltration, and size exclusion chromatography. Similar processes are disclosed in U.S. Pat. No. 5,981,735 by Thatcher et al. In these processes, the pH during alkaline lysis was carefully controlled at a point just below the empirically determined level that leads to permanent plasmid denaturation. The investigators claim that this allows extended incubation in alkali, presumably to maximize lysis and/or to degrade RNA without damaging plasmid. Impurities were reported to be <2% genomic DNA (by PCR), 0.2% RNA (by HPLC), <0.1% protein, and 2.5 EU/mg endotoxin. However, the process contains several undesirable elements, including use of RNase, bag depth filtration, column-based anion exchange, and size exclusion chromatography. Performing the controlled alkaline lysis requires carefully determining the ideal pH for a given combination of host, plasmid, and growth conditions, suggesting that this step may not be very robust.

As the above examples suggest, column chromatography is often a preferred element in plasmid purification. Anion exchange chromatography is well suited for separating plasmids from certain impurities such as proteins, because plasmids, like all nucleic acids, have a high negative charge density. Thus, many known plasmid purification processes include an anion exchange step. However, anion exchange chromatography is less suited for separating plasmids from other nucleic acids with similar negative charge densities, such as genomic DNA or RNA. Thus, anion exchange chromatography is frequently combined with another chromatographic step to achieve sufficiently pure plasmid. As discussed above, these may include size exclusion chromatography, reverse phase chromatography, hydrophobic interaction chromatography, and even additional anion exchange chromatography. Other chromatographic techniques are also known. For example, Wils and Ollivier, in WO 97/35002, disclose methods for purifying plasmids with ceramic hydroxyapatite. Comparable methods are disclosed by Yamamoto in U.S. Pat. No. 5,843,731. Ion-pair or matched ion chromatography may be used, as disclosed, for example, by Gjerde et al. in U.S. Pat. No. 5,986,085. Silica, glass beads, or glass fibers may also be used, as disclosed, for example, by Padhye et al. in U.S. Pat. No. 5,808,041, by Woodard et al. in U.S. Pat. No. 5,650,506, and by Woodard et al. in U.S. Pat. No. 5,693,785. Alternatively, magnetic beads or particles may be used, as disclosed, for example, by Reeve and Robinson in U.S. Pat. No. 5,665,554, and by Hawkins in U.S. Pat. No. 5,898,071. Affinity methods are also known, with examples being disclosed by Ji and Smith in U.S. Pat. No. 5,591,841, and by Cantor et al. in U.S. Pat. No. 5,482,836.

Despite the frequent use of column chromatography, there remain substantial limitations to this general technique. Chromatography resins are often expensive, and must be carefully packed into specially designed column hardware. Reproducibly packing large-scale chromatography columns is a significant challenge, as discussed by Rathore et al. (2003, *Biopharm International*, March, 30–40). Furthermore, in regards to plasmids, traditional chromatography resins typically offer relatively low binding capacities. For example, Levy et al. (2000, *Trends Biotechnol.* 18, 296–305) examined a variety of commercially available anion exchange resins and found that all exhibited plasmid binding capacities of about 5 mg/mL or less, with most exhibiting capacities of about 2 mg/mL or less. Moreover, accessibility to binding sites for large molecules like plasmids is mostly by diffusion and resins have a limited pressure drop resulting in low throughput, making these steps time consuming, costly and impractical.

Thus, it is desirable to develop a purification process that retains the advantages of column chromatography while avoiding its drawbacks. Use of membrane chromatography offers a potential solution. Membrane-based techniques typically offer substantially higher binding capacities, as well as very high flow rates. Expensive large-scale column hardware is not required. In addition, the difficulties associated with column packing are avoided, as well as the need for costly cleaning validation studies.

Certain previous investigators have disclosed membrane-based methods for purifying plasmids. For instance, Nieuwkerk et al., in U.S. Pat. No. 5,438,128, describe the use of an assembly containing a plurality of stacked microporous anion exchange membranes for purifying nucleic acids, including plasmids. However, their method is described for relatively small-scale purification of up to several hundred micrograms of plasmid. Furthermore, although the purified plasmid was stated to be RNA and protein free, there was no disclosure that the provided methods could substantially eliminate genomic DNA or endotoxin. Demmer and Nussbaumer, in U.S. Pat. No. 6,235,892, disclose a method of purifying nucleic acids, including plasmids, from a solution containing endotoxin, using a microporous weakly basic anion exchange membrane. Similarly, in WO 01/94573, Yang et al. claim a process involving two (or more) separate membranes, wherein one binds plasmid and the second binds endotoxin. The investigators state that their methods provide plasmid that is suitable for use in many pharmaceutical applications, but no data is provided to support this statement.

Thus, none of the disclosed membrane-based purification processes is demonstrably adequate for preparing substantially pure plasmid that is acceptable for pharmaceutical, veterinary, or agricultural applications. There is therefore a need for a purification process that employs membrane-based chromatographic separations, avoids column chromatography, and provides substantially pure plasmids or other biologically active molecules of interest.

SUMMARY

The present invention relates to a process for lysing cells in a controlled manner so as to efficiently separate insoluble components from a fluid lysate containing cellular components of interest, followed by membrane chromatographic techniques to purify the cellular components of interest. This process utilizes a unique lysis apparatus, ion exchange and, optionally, hydrophobic interaction chromatography membranes in cartridge form, and ultrafiltration. This process is optimized for the production of plasmids, but can be applied to any biologic product extracted from a cellular source. Advantageously, the process uses no animal derived products, organic solvents or carcinogens, and is rapid and cost effective. The process is operable to extract and purify plasmids from E. Coli bacteria, and provides material suitable for a variety of uses, including the clinical and commercial production of pharmaceutical products. The disclosed process uses a lysis apparatus, including a high shear, low residence-time mixer for advantageously mixing a cell suspension with a lysis solution, a hold time that denatures impurities, and an air-sparging bubble mixer that gently yet thoroughly mixes lysed cells with a neutralization/precipitation buffer and floats compacted precipitated cellular material. The floating precipitated cellular material can be readily removed from the remaining fluid by the simple expedient of draining or pumping the fluid from beneath the floating precipitate, allowing cellular components of interest to subsequently be purified from the fluid (preferably) or from the precipitate.

The method for producing a cellular component of interest from a cell population comprises subjecting the cell population to the disclosed cell lysis and separation apparatus and methods to prepare a clarified lysate. The cellular components of interest are purified from the clarified lysate by subjecting it to an ion exchange cartridge, optionally followed by a hydrophobic interaction cartridge. Following purification, ultrafiltration/diafiltration is performed to concentrate and desalt the substantially purified material. If desired, the purified material may then be subjected to sterile filtration to provide a sterile, substantially purified material.

The present invention offers numerous benefits over previously disclosed methods. In one aspect, the present invention discloses an improved way to mix a cell suspension with a lysis solution. Clearly, it is desirable to achieve complete mixing of a cell suspension with a lysis solution, so that substantially all of the cells become lysed and release the cellular components of interest into the lysate for subsequent purification. Incomplete mixing of a cell suspension with a lysis solution may result in a substantial portion of the cells remaining intact. This will result in suboptimal yields of the cellular components of interest, increasing product costs and requiring higher production scales to recover a desired amount of final product.

The current invention recognizes that low shear mixing of a cell suspension and a lysis solution is not necessary, even for the demanding application of lysing plasmid-containing cells with alkali. Thus, the current invention provides for methods of mixing a cell suspension and a lysis solution using a high shear, low residence-time mixing device. The high shear nature of the described method ensures substantially complete mixing of the cell suspension and the lysis solution. The low residence-time provided by the described method avoids subjecting cellular components released by the lysing cells to extended periods of high shear. In a preferred embodiment, the mixing is performed in a continuous flow-through mode, which provides substantial advantage in processing large volumes, and is particularly advantageous in controlling time of exposure to the lysis solution. Unlike static mixing, the present invention provides great process flexibility. Substantially complete mixing is not dependent on fluid flow rates, and the agitation rate of the mixing device is easily adjusted. Thus, one skilled in the art will readily recognize that fluid flow rates through the high shear, low residence-time mixing device can be varied over a wide range. This provides substantial freedom to increase the amount of material processed in a given time without modifying the apparatus.

In another aspect, the present invention discloses an improved method for mixing a cell lysate with one or more additional fluids while avoiding shearing of sensitive components. For example, whereas the present invention discloses that plasmid-containing cells may be mixed with an alkaline lysis solution under high shear conditions, it remains true that subsequent mixing steps involving the lysed cell solution must be performed under low shear conditions. In particular, it is common to mix alkaline lysates of plasmid-containing cells with a neutralizing and precipitating solution that simultaneously neutralizes the alkali and precipitates various cellular components. The neutralization prevents formation of permanently denatured plasmid, while the precipitation sequesters large amounts of genomic DNA, endotoxin, protein, lipids, lipopolysaccharides, cell wall and membrane components into the a flocculent solid material. It is well known that vigorous or high shear mixing at this step releases excessive amounts of genomic DNA, endotoxin, and other impurities into the plasmid-containing solution. These impurities are difficult to subsequently purify away from the biologically active plasmid. Thus, it is highly desirable to perform this step using a gentle, low shear mixing process. At the same time, it is necessary to achieve substantially complete mixing at this step. Otherwise, some portions of the plasmid will be subjected to alkali for excessive times and become permanently denatured. Similarly, insufficient mixing may lead to incomplete precipitation of cellular components, complicating subsequent efforts to prepare substantially purified plasmid.

As discussed above, previous investigators have attempted to address these needs using techniques such as static mixing or low shear batch mixing. The drawbacks to these techniques are described above and are readily apparent to one skilled in the art. The present invention discloses the use of a bubble mixer for mixing cell lysates with fluids such as neutralization/precipitation solutions. The present invention also discloses a bubble mixing device that may be used to perform the disclosed method. Advantageously, the method and device disclosed herein use gas bubbles to achieve thorough mixing of the fluids. Simultaneously, some of the gas bubbles become trapped in the resulting precipitated cellular components. This facilitates floating of the precipitated material, advantageously aiding its later separation from the fluid containing the cellular components of interest. This is a noteworthy benefit of the present invention.

Another aspect of the present invention provides integrated methods for preparing a clarified lysate containing cellular components of interest, as well as an apparatus useful for performing the methods. In this aspect, the individually disclosed methods described above are combined into a continuous process comprising: (1) mixing a cell suspension with a lysis solution using a high shear, low residence-time mixer; (2) passing the mixed cell suspension and lysis solution through a holding coil to provide a fixed exposure time sufficient to provide substantially complete cell lysis and genomic DNA denaturation; (3) mixing the lysed cells with a solution such as a neutralization/precipitation solution using a bubble mixer, thereby trapping gas bubbles with precipitated cellular components; and (4) collecting the resulting material into a settling tank.

Advantageously, these steps are performed as a continuous process, offering the operator substantial flexibility and ease of performance. In further embodiments, the material collected in the settling tank is held for a time sufficient to allow the precipitated cellular components to form a floating layer. Formation of this layer is aided by the entrapped bubbles introduced by the bubble mixer. Optionally, a vacuum may be applied to the material in the settling tank to further compact the precipitated cellular components and degas the fluid. Subsequently, the fluid maybe separated from the precipitated cellular components by pumping or draining it from beneath the precipitated cellular components. The resulting separated fluid comprises a clarified lysate that may then be subjected to various methods to substantially purify the cellular components of interest present in the lysate. An advantage of the disclosed invention is that flocculent precipitated cellular components are separated from the fluid without resorting to depth filtration or centrifugation.

In another aspect, the present invention discloses methods for purifying cellular components of interest from lysed cells. In a preferred embodiment, the cellular components of interest are plasmids, and the cells are plasmid-containing cells. The methods utilize ion exchange membrane purification, optionally followed by a second membrane purification that removes endotoxin and RNA, to provide a substantially purified product. Preferably, the ion exchange takes the form of anion exchange. Preferably, the second membrane purification takes the form of hydrophobic interaction. Additional steps such as ultrafiltration/diafiltration and sterile filtration may be performed to concentrate, desalt, and sterilize the cellular component of interest. Advantageously, the methods disclosed herein avoid the use of traditional column chromatography, which employs expensive chromatography resins and column hardware, is typically limited by poor binding capacity, and is typically limited to low fluid flow rates. In contrast, the membrane based purification methods disclosed herein offer reduced cost, high binding capacity, and high flow rates, resulting in a superior purification process. The purification process is further demonstrated to produce plasmid products substantially free of genomic DNA, RNA, protein, and endotoxin.

In a particularly preferred embodiment, all of the described aspects of the current invention are advantageously combined to provide an integrated process for preparing substantially purified cellular components of interest from cells. Again, the cells are most preferably plasmid-containing cells, and the cellular components of interest are most preferably plasmids. The substantially purified plasmids are suitable for various uses, including, but not limited to, gene therapy, plasmid-mediated therapy, as DNA vaccines for human, veterinary, or agricultural use, or for any other application that requires large quantities of purified plasmid. In this aspect, all of the advantages described for individual aspects of the present invention accrue to the complete, integrated process, providing a highly advantageous method that is rapid, scalable, and inexpensive. Enzymes and other animal-derived or biologically sourced products are avoided, as are carcinogenic, mutagenic, or otherwise toxic substances. Potentially flammable, explosive, or toxic organic solvents are similarly avoided.

One aspect of the present invention is an apparatus for isolating plasmid DNA from a suspension of cells having both plasmid DNA and genomic DNA. An embodiment of the apparatus comprises a first tank and second tank in fluid communication with a mixer. The first tank is used for holding the suspension cells and the second tank is used for holding a lysis solution. The suspension of cells from the first tank and the lysis solution from the second tank are both allowed to flow into the mixer forming a lysate mixture or lysate fluid. The mixer comprises a high shear, low residence-time mixing device with a residence time of equal to or less than about 1 second. In a preferred embodiment, the mixing device comprises a flow through, rotor/stator mixer or emulsifier having linear flow rates from about 0.1 L/min to about 20 L/min. The lysate-mixture flows from the mixer into a holding coil for a period of time sufficient to lyse the cells and forming a cell lysate suspension, wherein the lysate-mixture has resident time in the holding coil in a range of about 2–8 minutes with a continuous linear flow rate.

The cell lysate suspension is then allowed to flow into a bubble-mixer chamber for precipitation of cellular components from the plasmid DNA. In the bubble mixer chamber, the cell lysate suspension and a precipitation solution or a neutralization solution from a third tank are mixed together using gas bubbles, which forms a mixed gas suspension comprising a precipitate and an unclarified lysate or plasmid containing fluid. The precipitate of the mixed gas suspension is less dense than the plasmid containing fluid, which facilitates the separation of the precipitate from the plasmid containing fluid. The precipitate is removed from the mixed gas suspension to give a clarified lysate having the plasmid DNA, and the precipitate having cellular debris and genomic DNA.

In a preferred embodiment, the bubble mixer-chamber comprises a closed vertical column with a top, a bottom, a first, and a second side with a vent proximal to the top of the column. A first inlet port of the bubble mixer-chamber is on the first side proximal to the bottom of the column and in fluid communication with the holding coil. A second inlet port of the bubble mixer-chamber is proximal to the bottom on a second side opposite of the first inlet port and in fluid communication with a third tank, wherein the third tank is used for holding a precipitation or a neutralization solution. A third inlet port of the bubble mixer-chamber is proximal to the bottom of the column and about in the middle of the first and second inlets and is in fluid communication with a gas source the third inlet entering the bubble-mixer-chamber. A preferred embodiment utilizes a sintered sparger inside the closed vertical column of the third inlet port. The outlet port exiting the bubble mixing chamber is proximal to the top of the closed vertical column. The outlet port is in fluid communication with a fourth tank, wherein the mixed gas suspension containing the plasmid DNA is allowed to flow from the bubble-mixer-chamber into the fourth tank. The fourth tank is used for separating the precipitate of the mixed gas suspension having a plasmid containing fluid, and can also include an impeller mixer sufficient to provide uniform mixing of fluid without disturbing the precipitate. A fifth tank is used for a holding the clarified lysate or clarified plasmid containing fluid. The clarified lysate is then filtered at least once. A first filter has a particle size limit of about 5–10 μm and the second filter has a cut of about 0.2 μm.

Although gravity, pressure, vacuum, or a mixture thereof can be used for transporting: suspension of cells; lysis solutions; precipitation solutions; neutralization solutions; or mixed gas suspensions from any of the tanks to mixers, holding coils or different tanks, pumps are utilized in a preferred embodiments. In a more preferred embodiment, at least one pump having a linear flow rate of at least 0.1–1 ft/second is used.

In another specific embodiment, a Y-connector having a having a first bifurcated branch, a second bifurcated branch and an exit branch is used to contact the cell suspension and the lysis solutions before they enter the high shear, low residence-time mixing device. The first tank holding the cell suspension is in fluid communication with the first bifurcated branch of the Y-connector through the first pump and the second tank holding the lysis solution is in fluid communication with the second bifurcated branch of the Y-connector through the second pump. The high shear, low residence-time mixing device is in fluid communication with an exit branch of the Y-connector, wherein the first and second pumps provide a linear flow rate of about 0.1 to 2 ft/second for a contacted fluid exiting the Y-connector.

Another specific aspect of the present invention is a method of substantially separating plasmid DNA and genomic DNA from a bacterial cell lysate. The method comprises: delivering a cell lysate into a chamber; delivering a precipitation fluid or a neutralization fluid into the chamber; mixing the cell lysate and the precipitation fluid or a neutralization fluid in the chamber with gas bubbles forming a gas mixed suspension, wherein the gas mixed suspension comprises the plasmid DNA in a fluid portion (i.e. an unclarified lysate) and the genomic DNA is in a precipitate that is less dense than the fluid portion; floating the precipitate on top of the fluid portion; removing the fluid portion from the precipitate forming a clarified lysate, whereby the plasmid DNA in the clarified lysate is substantially separated from genomic DNA in the precipitate. In preferred embodiments: the chamber is the bubble mixing chamber as described above; the lysing solution comprises an alkali, an acid, a detergent, an organic solvent, an enzyme, a chaotrope, or a denaturant; the precipitation fluid or the neutralization fluid comprises potassium acetate, ammonium acetate, or a mixture thereof; and the gas bubbles comprise compressed air or an inert gas. Additionally, the decanted-fluid portion containing the plasmid DNA is preferably further purified with one or more purification steps selected from a group consisting of: ion exchange, hydrophobic interaction, size exclusion, reverse phase purification, endotoxin depletion, affinity purification, adsorption to silica, glass, or polymeric materials, expanded bed chromatography, mixed mode chromatography, displacement chromatography, hydroxyapatite purification, selective precipitation, aqueous two-phase purification, DNA condensation, thiophilic purification, ion-pair purification, metal chelate purification, filtration through nitrocellulose, or ultrafiltration.

A preferred specific aspect, a method for isolating a plasmid DNA from cells comprising: mixing a suspension of cells having the plasmid DNA and genomic DNA with a lysis solution in a high-shear-low-residence-time-mixing-device for a first period of time forming a cell lysate fluid; incubating the cell lysate fluid for a second period of time in a holding coil forming a cell lysate suspension; delivering the cell lysate suspension into a chamber; delivering a precipitation/neutralization fluid into the chamber; mixing the cell lysate suspension and the a precipitation/neutralization fluid in the chamber with gas bubbles forming a gas mixed suspension, wherein the gas mixed suspension comprises an unclarified lysate containing the plasmid DNA and a precipitate containing the genomic DNA, wherein the precipitate is less dense than the unclarified lysate; floating the precipitate on top of the unclarified lysate; removing the precipitate from the unclarified lysate forming a clarified lysate, whereby the plasmid DNA is substantially separated from genomic DNA; precipitating the plasmid DNA from the clarified lysate forming a precipitated plasmid DNA; and resuspending the precipitated plasmid DNA in an aqueous solution.

DETAILED DESCRIPTION OF PREFERRED EMBODIMENTS

Figure 1:
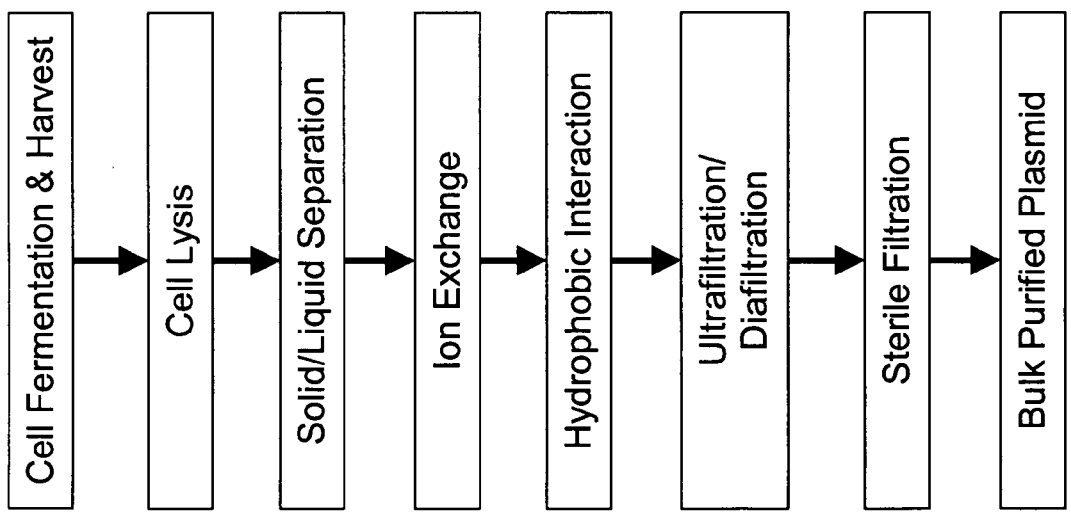
FIG. 1 is a summary flowchart of the steps described herein for isolating a cellular component of interest such as a plasmid, beginning with cell fermentation and leading to bulk purified product.

It will be readily apparent to one skilled in the art that various substitutions and modifications may be made in the invention disclosed herein without departing from the scope and spirit of the invention.

As used herein, the term "a" or "an" may refer to one or more than one. As used herein in the claims, when used in conjunction with the word "comprising", the words "a" or "an" may mean one or more than one. As used herein, "another" may mean at least a second or more.

As used herein, the term "alkali" refers to a substance that provides a pH greater than about 8 when a sufficient quantity of the substance is added to water. The term alkali includes, but is not limited to, sodium hydroxide (NaOH), potassium hydroxide (KOH), or lithium hydroxide (LiOH).

As used herein, the term "detergent" refers to any amphipathic or surface-active agent, whether neutral, anionic, cationic, or zwitterionic. The term detergent includes, but is not limited to, sodium dodecyl sulfate (SDS), Triton® (polyethylene glycol tert-octylphenyl ether, Dow Chemical Co., Midland, Mich.), Pluronic® (ethylene oxide/propylene oxide block copolymer, BASF Corp., Mount Olive, N.J.), Brij® (polyoxyethylene ether, ICI Americas, Bridgewater, N.J.), 3-[(3-cholamidopropyl)dimethylammonio]-1-propanesulfonate (CHAPS), 3-[(3-cholamidopropyl)dimethylammonio]-2-hydroxy-1-propanesulfonate (CHAPSO), Tween® (polyethylene glycol sorbitan, ICI Americas, Bridgewater, N.J.), bile acid salts, cetyltrimethylammonium, N-lauroylsarcosine, Zwittergent® (n-alkyl-N,N-dimethyl-3-ammonio-1-propanesulfonate, Calbiochem, San Diego, Calif.), etc.

As used herein, the term "ion exchange" refers to a separation technique based primarily on ionic interactions between a molecule or molecules of interest, and a suitable ion exchange material. Although the ion exchange material may most commonly take the form of a chromatography resin or membrane, it may be any material suitable for performing separations based on ionic interactions. The term ion exchange encompasses anion exchange, cation exchange, and combinations of both anion and cation exchange.

As used herein, the term "anion exchange" refers to a separation technique based primarily on ionic interactions between one or more negative charges on a molecule or molecules of interest, and a suitable positively charged anion exchange material. Although the anion exchange material may most commonly take the form of a chromatography resin or membrane, it may be any material suitable for performing separations based on the described ionic interactions.

As used herein, the term "cation exchange" refers to a separation technique based primarily on ionic interactions between one or more positive charges on a molecule or molecules of interest, and a suitable negatively charged cation exchange material. Although the cation exchange material may most commonly take the form of a chromatography resin or membrane, it may be any material suitable for performing separations based on the described ionic interactions.

As used herein, the terms "hydrophobic interaction" and "HIC" refer to a separation technique based primarily on hydrophobic interactions between a molecule or molecules of interest, and a suitable primarily hydrophobic or hydrophillic material. Although the primarily hydrophobic or hydrophilic material may most commonly take the form of a chromatography resin or membrane, it may be any material suitable for performing separations based on hydrophobic interactions.

As used herein, the term "plasmid" refers to any distinct cell-derived nucleic acid entity that is not part of or a fragment of the host cell's primary genome. As used herein, the term "plasmid" may refer to either circular or linear molecules composed of either RNA or DNA. The term "plasmid" may refer to either single stranded or double stranded molecules, and includes nucleic acid entities such as viruses and phages.

As used herein, the term "genomic DNA" refers to DNA derived from the genome of a host cell. As used herein, the term includes DNA molecules comprising all or any part of the host cell primary genome, whether linear or circular, single stranded or double stranded.

As used herein, the term "endotoxin" refers to lipopolysaccharide material that is derived from Gram-negative bacteria and that causes adverse effects in animals. Endotoxin can typically be detected by the *limulus amebocyte* lysate ("LAL") assay.

As used herein, the term "high shear, low residence-time mixer" describes any device that subjects a fluid or fluids, such as biological fluid or fluids (containing, among others, plasmids, cell suspension, lysis solution, proteins, peptides, amino acids, nucleic acids, others, or a mixture thereof) to brief periods of high shear, at a shear rate of at least 4000/sec, resulting in substantially complete mixing of all elements and components of the fluid or fluids in about 1 second or less.

As used herein, the term "chromatography" includes any separation technique that involves a molecule or molecules interacting with a matrix. The matrix may take the form of solid or porous beads, resin, particles, membranes, or any other suitable material. Unless otherwise specified, chromatography includes both flow-through and batch techniques.

As used herein, the term "precipitation" refers to the process whereby one or more components present in a solution, suspension, emulsion or similar state form a solid material.

As used herein, the terms "precipitation solution" and "precipitating solution" refer to any solution, suspension, or other fluid that induces precipitation. Unless otherwise specified, a precipitation solution may also provide neutralization.

As used herein, the term "neutralization" refers to a process whereby the pH of an acidic or an alkaline material is brought near to neutrality. Typically, neutralization brings the pH into a range of about 6 to about 8.

As used herein, the terms "neutralization solution" and "neutralizing solution" refer to any solution, suspension, or other fluid which results in neutralization when mixed with an acidic or an alkaline material. Unless otherwise specified, a neutralization solution may also provide precipitation.

As used herein, the term "neutralization/precipitation solution" refers to any solution, suspension or other fluid that provides both neutralization and precipitation.

As used herein, the term "cellular components" includes any molecule, group of molecules, or portion of a molecule derived from a cell. Examples of cellular components include, but are not limited to, DNA, RNA, proteins, plasmids, lipids, carbohydrates, monosaccharides, polysaccharides, lipopolysaccharides, endotoxins, amino acids, nucleosides, nucleotides, and so on.

As used herein, the term "membrane," as used with respect to chromatography or separations methods and materials, refers to any substantially continuous solid material having a plurality of pores or channels through which fluid can flow. A membrane may, without limitation, comprise geometries such as a flat sheet, pleated or folded layers, and cast or cross-linked porous monoliths. By contrast, when used in reference to a cell component, the term "membrane" refers to all or a part of the lipid-based envelope surrounding a cell.

As used herein, the term "bubble mixer" refers to any device that uses gas bubbles to mix two or more unmixed or incompletely mixed materials.

As used herein, the term "cell suspension" refers to any fluid comprising cells, cell aggregates, or cell fragments.

As used herein, the term "cell lysate" refers to any material comprising cells, wherein a substantial portion of the cells have become disrupted and released their internal components.

As used herein, the term "lysis solution" refers to any solution, suspension, emulsion, or other fluid that causes lysis of contacted cells.

As used herein, the term "clarified lysate" refers to a lysate that has been substantially depleted of visible particulate solids.

As used herein, the term "macroparticulate" refers to solid matter comprising particles greater than or about 100 μm in diameter.

As used herein, the term "microparticulate" refers to solid matter comprising particles less than about 100 μm in diameter.

As used herein, the terms "ultrafiltration" and "UF" refer to any technique in which a solution or a suspension is subjected to a semi-permeable membrane that retains macromolecules while allowing solvent and small solute molecules to pass through. Ultrafiltration may be used to increase the concentration of macromolecules in a solution or suspension. Unless otherwise specified, the term ultrafiltration encompasses both continuous and batch techniques.

As used herein, the terms "diafiltration" and "DF" refer to any technique in which the solvent and small solute molecules present in a solution or a suspension of macromolecules are removed by ultrafiltration and replaced with different solvent and solute molecules. Diafiltration may be used to alter the pH, ionic strength, salt composition, buffer composition, or other properties of a solution or suspension of macromolecules. Unless otherwise specified, the term diafiltration encompasses both continuous and batch techniques.

As used herein, the terms "ultrafiltration/diafiltration" and "UF/DF" refer to any technique or combination of techniques that accomplishes both ultrafiltration and diafiltration, either sequentially or simultaneously.

One aspect of the present invention relates to a method for lysing cells in a controlled manner so as to extract cellular components of interest. The cells may be any cells containing cellular components of interest. Preferably, they are microbial cells. More preferably, they are *E. coli* cells. The cells may be produced or generated by any means, but are preferably generated by fermentation. Methods for fermenting cells are well known to those skilled in the art. The present invention may be employed to extract any cellular component of interest from cells. Preferably, these will be macromolecules such as plasmids or proteins. More preferably, they are plasmids. Thus, in one preferred embodiment, the present invention relates to an advantageous method for lysing plasmid-containing *E. coli* cells so as to extract the plasmids.

Another aspect of the present invention relates to a method for purifying cellular components of interest from a cell lysate. The cell lysate may be a lysate of any type of cells containing the cellular components of interest. Further, the cell lysate may be produced by any means known to one of skill in the art. Preferably, the lysate comprises lysed plasmid-containing cells. More preferably, the lysate comprises plasmid-containing cells lysed with alkali, detergent, or a combination thereof. Preferably, the cellular components of interest are plasmids.

FIG. 1 presents an overall summary of an especially preferred embodiment that combines all aspects of the present invention. In the first step, cells of interest are produced and harvested. Preferably, the cells are produced by fermentation. Any fermentation method may be used, and it is well within the abilities of one skilled in the art to prepare sufficient quantities of the cells of interest. In particularly preferred embodiments, the cells are *E. coli* containing a high copy number plasmid of interest, and the plasmid-containing cells are fermented to high density using batch or fed batch techniques. Methods for preparing such plasmid-containing *E. coli* cells and performing such batch or fed-batch fermentation are well known to those skilled in the art. The cells are harvested by any means, such as centrifugation or filtration, to form a cell paste. Such harvesting methods are well known to those skilled in the art. Furthermore, those skilled in the art will recognize that harvested cells or cell paste may be processed immediately, or stored in a frozen or refrigerated state for processing at a later date.

In the second step, cells are lysed to release their contents, including the cellular components of interest, into solution. Preferred methods for performing this step are disclosed herein, and are described in detail below.

In the third step, solid cell debris and precipitated cellular components are separated from a clarified lysate. Preferred methods for performing this step are disclosed herein, and are described in detail below.

In the fourth step, solutions containing the cellular components of interest are subjected to ion exchange chromatography. Preferably, this is performed using a membrane-based approach. Preferably, this is anion exchange membrane chromatography. Specific methods for performing this step are further disclosed in detail below.

In the fifth step, the partially purified material resulting from ion exchange chromatography is subjected to hydrophobic interaction chromatography. Preferably, this is performed using a membrane-based approach. Specific methods for performing this step are further disclosed in detail below. In certain embodiments, this step may be omitted.

In the sixth step, the material resulting from hydrophobic interaction chromatography (if performed) or from ion exchange chromatography (if HIC is omitted) is subjected to ultrafiltration and diafiltration, to concentrate the cellular components of interest, and to remove excess salts from the solution. Use of ultrafiltration/diafiltration is well known to those of skill in the art, especially for biological macromolecules such as proteins or plasmids.

In the seventh step, the concentrated and desalted product is optionally subjected to sterile filtration, for example to render it suitable for pharmaceutical uses. Again, methods for performing this step are well within the knowledge of those skilled in the art.

The result of these steps is a bulk preparation of substantially purified cellular components of interest. Preferably, these cellular components are plasmids. More preferably, they are substantially free of genomic DNA, RNA, protein, and endotoxin.

Figure 2:
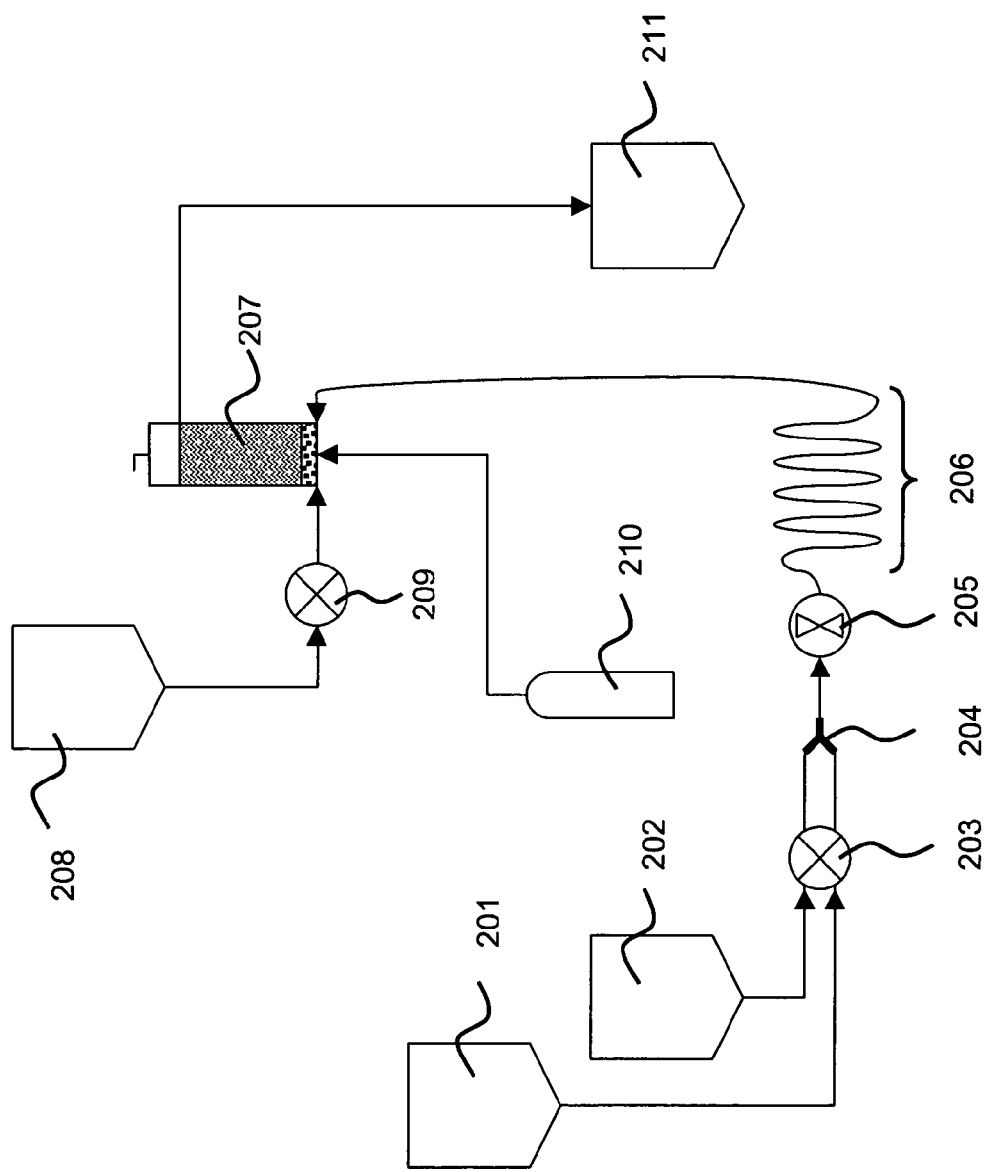
FIG. 2 is a diagram of the apparatus used herein for continuous cell lysis and neutralization/precipitation.

FIG. 2 is a diagram of the apparatus used for cell lysis. In particular, the apparatus is suitable for a continuous process involving contacting a cell suspension with a lysis solution, mixing the contacted fluids using a high shear, low residence-time mixer, passing the lysate-mixture through a holding coil for a determined time sufficient to provide substantially complete cell lysis and genomic DNA denaturation without permanently denaturing cellular components of interest, mixing the resulting cell lysate with a precipitating solution using a bubble mixer, and collecting the resulting material in a settling tank.

Cells containing a biologically active molecule of interest are made into a suitable suspension and loaded into a tank (201 in FIG. 2). The cells may be suspended in any suitable solution. Preferably the cells are plasmid-containing *E. coli* cells. The suspension solution preferably contains a moderate concentration of buffer, a moderate concentration of a chelating agent, or both. Most preferably, the suspension solution comprises about 25 mM Tris and about 10 mM Na$_2$EDTA, at a pH of about 8. In a preferred embodiment, the cell suspension is prepared by suspending a known weight of cell paste with a known weight of suspension buffer. Preferably, one part cell paste is resuspended in about 4–10 parts buffer, more preferably with about 6–8 parts buffer. The optical density of the resulting cell suspension is preferably about 50–80 OD$_{600}$ units. More preferably it is about 60–70 OD$_{600}$ units.

A lysis solution is loaded into a tank (202 in FIG. 2). The lysis solution preferably contains one or more lysis agents, such as an alkali, an acid, an enzyme, an organic solvent, a detergent, a chaotrope, a denaturant, or a mixture of two or more such agents. More preferably, the lysis solution comprises an alkali, a detergent, or a mixture thereof. Suitable alkalis include, but are not limited to, NaOH, LiOH, or KOH. Detergents may be nonionic, cationic, anionic, or zwitterionic. Suitable detergents include, but are not limited to, SDS, Triton®, Tween®, Pluronic®, Brij®, and CHAPS, CHAPSO, bile acid salts, cetyltrimethylammonium, N-lauroylsarcosine, and Zwittergent®. Selection of suitable alkali or detergent will be well within the ordinary skill of the art. In a preferred embodiment, the lysis solution comprises NaOH and SDS. The NaOH concentration is preferably about 0.1 to about 0.3 N, and more preferably about 0.2 N. The SDS concentration is preferably about 0.1% to about 5%, and more preferably about 1%.

Cell suspension and lysis solution are retrieved from tanks 201 and 202 (respectively) using a pump (203 in FIG. 2), and brought into contact through a "Y" connector (204 in FIG. 2). In a preferred embodiment, equal volumes of cell suspension and lysis solution are pumped at equal flow rates using a dual head pump, as shown. However, those of skill in the art will recognize that cell suspension and lysis solutions of different volumes may be pumped at different rates, using individual pumps, if so desired. Such variations are well within the scope of the current invention. In a preferred embodiment, cell suspension and lysis solution are simultaneously pumped through a dual head pump at a linear flow rate of about 0.1–1 ft/s, more preferably about 0.2–0.5 ft/s. The contacted fluids preferably exit the "Y" connector at about 0.2–2 ft/s, more preferably about 0.4–1 ft/s.

After exiting the "Y" connector, the contacted cell suspension and lysis solution are passed through a high shear, low residence-time mixer (205 in FIG. 2). The mixer may be any device that provides rapid, high shear mixing while minimizing the residence time during which a given portion of the fluids are exposed to high shear. Preferably, the device mixes in a flow through mode (as opposed to a batch mode). In a preferred embodiment, the mixer is a rotor/stator mixer or an emulsifier. Those of skill in the art will recognize that a variety of such high shear, low residence-time mixers are commercially available. Such mixers are generally characterized by their ability to subject fluids to high shear microenvironments for very short periods of time, typically less than or about one second. Use of any such mixers is well within the scope of the present invention. In a preferred embodiment, the mixer is a Silverson L4R rotor/stator mixer fitted with a standard Emulsor screen and an In-line assembly (Silverson Machines, East Longmeadow, Mass.). In this embodiment, the rotor is preferably operated at a speed of 500–900 rpm, more preferably at a speed of 700–800 rpm. Such a mixer is suitable for processing a wide volume of cell suspensions. The L4R model by example can process fluids at flow rates from about 0.1 to about 20 L/min. However, one skilled in the art will recognize that larger scale mixers may be substituted for processing substantially greater volumes of cell suspension. Such substitution will be readily accomplished by one skilled in the art with no more than ordinary experimentation.

An advantage of using a high shear, low residence-time mixer, as provided herein, is that high shear is applied virtually instantaneously on two or more fluids, which provides superior mixing with a very short residence-time. Preferably, the residence-time will be less than or about one second. More preferably, the resident-time will be less than or about 100 ms. This short residence-time ensures that extracted cellular components are not deteriorated by excessive exposure to high shear conditions. A further advantage is that the mixers provided herein can readily accommodate different fluid flow rates, and provide the flexibility of adjustable speed mixing rotors. Such mixers are thus more flexible and useful than other in-line mixers such as static mixers. It is a novel finding of the present invention that the use of such high shear mixers is not detrimental when performing lysis procedures that were previously considered shear sensitive, such as when lysing plasmid-containing cells with alkali and detergent.

Material exiting the high shear, low residence-time mixer next passes through a holding coil (206 in FIG. 2). This coil comprises a length of tubing sufficient to provide that the fluid passes through the coil for a determined time. The function of the coil is to provide sufficient and consistent contact time between the cells and the lysis agent(s) to ensure substantially complete lysis. At the same time, the coil ensures that contact time is not so long as to have negative consequences. In a preferred embodiment, where the cells are plasmid-containing cells and the lysis solution comprises an alkali, it is desirable to ensure that exposure to alkali lasts long enough to achieve substantially complete cell lysis as well as substantially complete denaturation of proteins, genomic DNA, and other cellular components. However, it is also desirable that exposure to alkali not be so prolonged as to result in substantial amounts of permanently denatured plasmid. The holding coil provided in the present apparatus allows this contact time to be controlled. Preferably this contact time is about 2 to about 10 minutes, more preferably about 4 to about 6 minutes. The desired contact time may be provided by a suitable combination of coil length, coil inner diameter (ID), and linear flow rate. Selecting a suitable combination of these parameters will be well within the ability of one skilled in the art. In a preferred embodiment, the length and diameter of the holding coil are such that the desired exposure time is achieved when lysed cells are flowed through at the desired rate. Preferably, the holding coil is about 50 feet in length, with an inner diameter of about 0.625 inches. In this embodiment, the lysed cells preferably exit the high shear, low residence-time mixer and pass through the holding coil at about 0.17 ft/s, providing a contact time of about 5 minutes.

Figure 3:
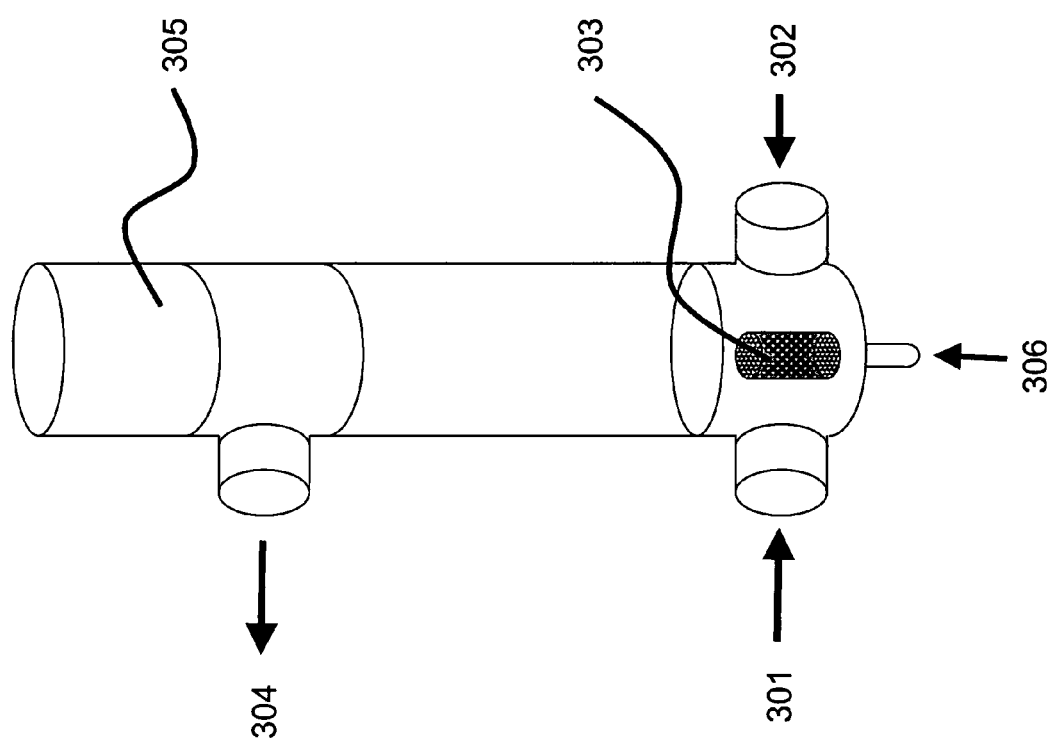
FIG. 3 is a diagram of the bubble mixer disclosed herein.

Lysed cells exiting the holding coil enter a bubble mixer (207 in FIG. 2). Simultaneously, a pump (209 in FIG. 2) delivers a neutralization/precipitation solution from a tank (208 in FIG. 2) into the bubble mixer. Also simultaneously, compressed gas from a tank (210 in FIG. 2) is sparged into the bottom of the bubble mixer. As the lysed cell solution enters the bubble column mixer, at least one additional solution is added. This may be a neutralization solution, a precipitation solution, or a combination thereof, that is the neutralization/precipitation solution. The determining factor of a solution to selectively precipitation unwanted or wanted cellular components is based upon total ionic concentration, and the ion or ions selected. Typically acetate salts are used for this purpose. The type of salt and concentration will also have an effect on the final pH of the resulting mixture. The pH of the solution may further be controlled through the addition of an acid, such as acetic acid. This acid may be added to the neutralizing solution or be directly added as an additional port on the bubble column mixer into the process stream to achieve independent control of neutralization and precipitation. In some cases it is advantageous to neutralize the mixture first, and precipitate at a later step, if further additions are desired, such as compaction agents. Under certain circumstances, it is advantageous to determine through calculation and experimental procedure a single solution (neutralization/precipitation solution) with the appropriate ions, ion strength, and final pH that can accomplish both the functions of neutralization of the lysed cell solution, as well as selectively precipitate certain cellular components. FIG. 3 shows a detailed diagram of a preferred embodiment of the bubble mixer. As shown, lysed cells enter the mixer at the bottom from one side (301 in FIG. 3), while neutralization/precipitation solution enters at the bottom from the opposite side (302 in FIG. 3). Compressed gas (306 in FIG. 3) is sparged in through a sintered sparger positioned approximately at the point where the fluid streams meet (303 in FIG. 3). Lysed cells and neutralization solution flow vertically up a column and exit through an outlet port on the side near the top (304 in FIG. 3). The passage of the gas bubbles through the vertical column of liquid serves to mix the lysed cells with the neutralization/precipitation solution. An advantage of the present invention is that the mixing provided by the rising gas bubbles is thorough but sufficiently gentle to avoid excessive fragmentation of sensitive components such as genomic DNA or endotoxins. As the neutralization/precipitation solution mixes with the cell lysate, cellular components become precipitated. A further advantage of the present invention is that some of the gas bubbles become trapped in the resulting precipitate, facilitating its later separation from the fluid fraction. A snorkel is provided at the top of the bubble mixer to vent excess gas (305 in FIG. 3).

In the embodiment used in the examples provided, the bubble mixer has the following dimensions: the lower inlet ports are 0.625 inch in in ternal diameter ("ID"); the sintered sparger is 1 inch tall with a diameter of 0.5 inch; the actual column area where mixing occurs is 1.375 inches ID and 24 inches tall; the outlet port is 1.375 inches ID; and the snorkel provided for excess gas and any foam is 12 inches tall with a 1.375 inch ID. However, one skilled in the art will recognize that larger or smaller scale mixers or alternate dimensions or geometries may be substituted for processing different volumes of solutions or solutions with differing properties such as, but not limited to, viscosity, density, and others. One skilled in the art will also recognize that various means for introducing gas bubbles may be used. As a non-limiting example, in place of a sintered sparger, the gas may be introduced through a plurality of small holes engineered into the walls, sides, or bottom of the mixer. Such substitutions will be readily accomplished by one skilled in the art, and are within the scope of the present invention.

It will be readily apparent to one skilled in the art that the bubble mixer provided in the present invention is beneficial for mixing any fluid of interest with one or more additional fluids. Examples of fluids of interest include, but are not limited to, cell suspensions, cell lysates, and fluids containing cellular components of interest. Examples of additional fluids include, but are not limited to, buffer solutions, salt solutions, lysis solutions, neutralization solutions, precipitation solutions, neutralization/precipitation solutions, and so on. Any number of fluids can be mixed, simply by providing an appropriate number of inlet ports. Thus, while two inlet ports are a preferred embodiment, one skilled in the art may readily provide a bubble mixer comprising three or more inlet ports, permitting mixing of three or more fluids. Such modifications are clearly encompassed within the current invention. Furthermore, one skilled in the art will recognize that the precise geometry and design of the bubble mixer provided herein may be readily altered. Again, such alterations are within the scope of the current invention.

The bubble mixer provided herein is particularly beneficial in mixing a cell lysate and a neutralizing/precipitating solution without excessively shearing sensitive components. In a preferred embodiment, the cell lysate comprises plasmid-containing cells lysed with an alkali, a detergent, or a mixture thereof, and the neutralizing/precipitating solution neutralizes the alkali and precipitates cellular components such as proteins, membranes, endotoxins, and genomic DNA. Preferably, the alkali is NaOH, the detergent is SDS, and the neutralization/precipitation solution comprises potassium acetate, ammonium acetate, acetic acid, or a combination thereof. More preferably, the neutralization/precipitation solution comprises an unbuffered solution containing about 1 M potassium acetate and about 7 M ammonium acetate. In contrast to the traditional neutralization/precipitation solution comprising about 3 M potassium acetate at a pH of about 5, this preferred neutralization/precipitation solution offers at least two advantages. First, after mixing with an alkaline lysate, the pH of the resulting crude lysate is about 8. This is preferable to the acidic pH provided by the traditional neutralization/precipitation solution, since it is well known that prolonged incubation of plasmids and other DNAs in acidic conditions can lead to depurination. A second advantage is that the high concentration of ammonium acetate provided in the preferred neutralization/precipitation solution helps to precipitate excess RNA from the crude lysate solution, which aids in obtaining a substantially purified plasmid product. This RNA precipitation is enhanced at lower temperatures. Hence, in a preferred embodiment, the neutralization/precipitation solution is provided in a chilled form at about 2–8° C. A particular advantage of the bubble mixer and the associated mixing methods disclosed herein is that alkaline lysates of plasmid-containing cells may be mixed with neutralization/precipitation solutions in a manner which avoids excessive release of genomic DNA and endotoxins into the plasmid-containing solution. A further advantage is that as the bubbles mix the fluids, a portion of the bubbles become substantially trapped in the precipitated material. These entrapped gas bubbles aid in floating the precipitated material, facilitating its later separation from the clarified lysate, as provided in detail below.

One skilled in the art will be able to determine suitable rates for flowing solutions through the bubble mixer using no more than ordinary experimentation. Preferably, lysed cells and neutralization/precipitation solution are flowed into the bubble mixer at equal rates of about 0.1–1 ft/s each, more preferably at about 0.2–0.5 ft/s each. One skilled in the art will be able to readily determine suitable rates for flowing gas through the bubble mixer. Preferably, gas flow rates are at least about 1 standard liter per minute (slpm), more preferably at least about 2 slpm. Any suitable gas may be used, including, but not limited to, air, nitrogen, argon, carbon dioxide, and so on. Preferably the gas is filtered compressed air. However, in certain applications, it may be preferable to use an inert gas such as nitrogen or argon, especially if any of the solutions or any components of the solutions are determined to be oxygen sensitive. Use of such inert gases is within the scope of the current invention.

With reference to FIG. 2, the slurry of fluid cell lysate and precipitated cellular components exits the bubble mixer and is collected in a settling tank (211 in FIG. 2). The slurry may be held in the settling tank for a time sufficient to achieve substantially complete separation of the precipitated cellular components from the fluid cell lysate. Preferably, the precipitated components float, aided by the entrapped gas bubbles introduced by the bubble mixer. In a preferred embodiment, a vacuum may be applied to the settling tank. This procedure partially compacts the floating flocculent precipitate, aiding its subsequent separation and also allowing a greater percentage of clarified cell lysate to be recovered in later steps. As a further advantage, application of a vacuum at this step aids in degassing the lysate, which is desirable prior to subsequent purification steps. Preferably, the applied vacuum is at least about 15 inches of Hg, more preferably at least about 20 inches of Hg, most preferably at least about 25 inches of Hg. In a preferred embodiment, the slurry is held in the settling tank for about 6 to about 24 hours, more preferably for about 12–18 hours. Preferably, the vacuum is maintained throughout this holding period. Preferably, the slurry is also chilled to less than about 15° C. during the holding period, more preferably to about 2–8° C., to aid in precipitating RNA or other impurities. In one embodiment, the crude cell lysate may be gently mixed during the holding period, such as by an impeller mixer operated at a low rpm, sufficient to provide uniform mixing and cooling of the fluid without disturbing the flocculent precipitate. Selecting suitable equipment and operating parameters to achieve these desired mixing conditions will be well within the abilities of one skilled in the art.

A variety of modifications may be made to the apparatus described in FIG. 2, without departing from the spirit of the present invention. For example, the tanks shown in FIG. 2 may be any type of container suitable for holding the indicated materials. Examples of suitable containers include, but are not limited to, disposable or reusable plastic bags as well as rigid vessels made of plastic, stainless steel, or other suitable material. Similarly, although it is convenient and preferable to transport fluids using pumps, as shown, other methods may also be used, including but not limited to flowing by gravity, pressure, vacuum, or any other means. In addition, although a "Y" connector is preferred for contacting the cell suspension and the lysis solution, any method that delivers the cell suspension and the lysis solution to the high shear, low-residence time mixing device in the appropriate proportions may be used. As an example, and without limiting the scope of the present invention, the cell suspension and the lysis solution may be separately fed into the high shear, low-residence time mixing device through independent intake ports. Furthermore, although it is preferable to use a compressed gas tank to introduce gas bubbles into the bubble mixer, any method that provides gas flow adequate to achieve the desired mixing may be used. All such modifications to the described apparatus are within the scope of the present invention.

Figure 4:
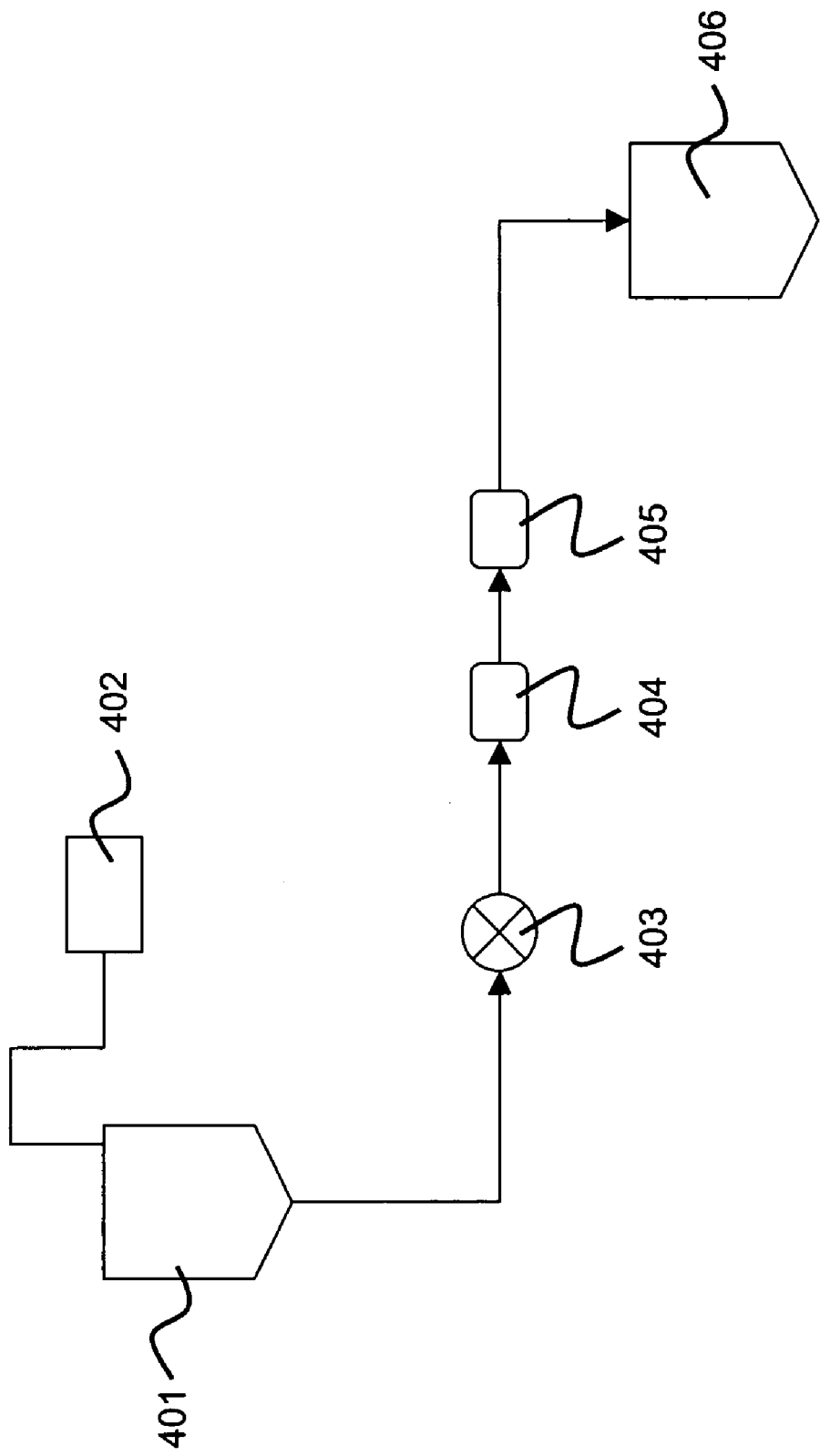
FIG. 4 is a diagram of solid/liquid separation.

FIG. 4 provides a schematic diagram of solid/liquid separation. The settling tank shown as tank 211 in FIG. 2 is relabled in FIG. 4 as tank 401, and contains the crude cell lysate solution, with the floating precipitated cellular components. If used, vacuum is applied using a vacuum pump (402 in FIG. 4), as described above. Prior to beginning solid/liquid separation, any vacuum applied to the tank is carefully released. Fluid cell lysate is then collected from the tank using a pump (403 in FIG. 4). At this point, the fluid comprises a clarified lysate that is substantially free of cellular debris and macroparticulate solid matter. It is an advantage of the present invention that the clarified lysate is separated from the precipitated cellular components without resorting to centrifugation or macroparticulate filtration techniques. Such techniques require expensive equipment, and are often impractical and difficult to scale up. Furthermore, subjecting the precipitated cellular components to centrifugation or macrofiltration may lead to excessive release of genomic DNA, endotoxins, or other components into the clarified lysate. These can be difficult to subsequently separate from cellular components of interest in the clarified lysate, particularly in the preferred case where the cellular components of interest are plasmids. The present invention avoids these undesirable events.

Thus the present invention provides for advantageously separating a clarified cell lysate from precipitated cellular components. One skilled in the art will recognize that various purification techniques may be applied to either the clarified lysate or the precipitated cellular components provided by the above methods. Such purification techniques may be used to provide a substantially pure preparation of a cellular component of interest. The cellular component of interest may be purified from the precipitated cellular components provided above, or from the clarified lysate. Preferably, the cellular component of interest is purified from the clarified lysate. Preferably, the cellular component of interest is a plasmid that is present in the clarified lysate. In this preferred embodiment, any of a variety of purification procedures may be applied, either individually or in combination, to provide substantially purified plasmids. Such purification procedures include, but are not limited to, ion exchange, hydrophobic interaction, size exclusion, reverse phase purification, endotoxin depletion, affinity purification, adsorption to silica, glass, or polymeric materials, expanded bed chromatography, mixed mode chromatography, displacement chromatography, hydroxyapatite purification, selective precipitation, aqueous two-phase purification, DNA condensation, thiophilic purification, ion-pair purification, metal chelate purification, filtration through nitrocellulose, and ultrafiltration. One skilled in the art will be able to apply any known purification technique to a clarified lysate prepared according to the present invention, with no more than ordinary experimentation.

In the preferred embodiment wherein the cellular components of interest are present in the clarified lysate, it is advantageous to pass the clarified lysate through one or more microparticulate filters and collect it in a holding tank (406 in FIG. 4). Preferably, clarified lysate is retrieved from tank 401 and subjected to microparticulate filtration as a continuous operation. Alternately, clarified lysate may be retrieved from tank 401 and collected in an intermediate vessel. Microparticulate filtration may then be performed as an independent operation. Preferably, the settling tank 401 is fitted with a sight glass, allowing an operator to observe the position of the liquid level and the precipitated cellular components. Pumping of material from the tank is monitored visually, and halted before the precipitated cellular components enter the line. This prevents clogging of the subsequent microparticulate filters. Preferably, about one to about three microparticulate filters may be used in succession, with the first filter removing larger particles, and subsequent filters removing successively smaller particles. As shown in FIG. 4, two filters in series are preferred. In a preferred embodiment, the first filter (404 in FIG. 4) is a pre-filter with a particle size limit of about 5 to about 10 µm, more preferably about 10 µm. The second filter (405 in FIG. 4) is preferably a membrane filter with a cut-off of about 0.2 µm. However, one skilled in the art will recognize that details such as the number of filters used, as well as their particle size limits, may be readily varied. Furthermore, one skilled in the art will be able to determine situations where no filtration is required, in which case the filter units shown in FIG. 4 may be omitted. Any combination of filters, including no filters at all, is contemplated to be within the scope of the present invention.

As before, various modifications may be made to the apparatus depicted in FIG. 4. Such modifications include, but are not limited to, alternate means for transporting fluids, alternate means for applying a vacuum, and alternate containers for holding the described materials. All such modifications are within the abilities of one skilled in the art, and are within the scope of the present invention.

Figure 5:
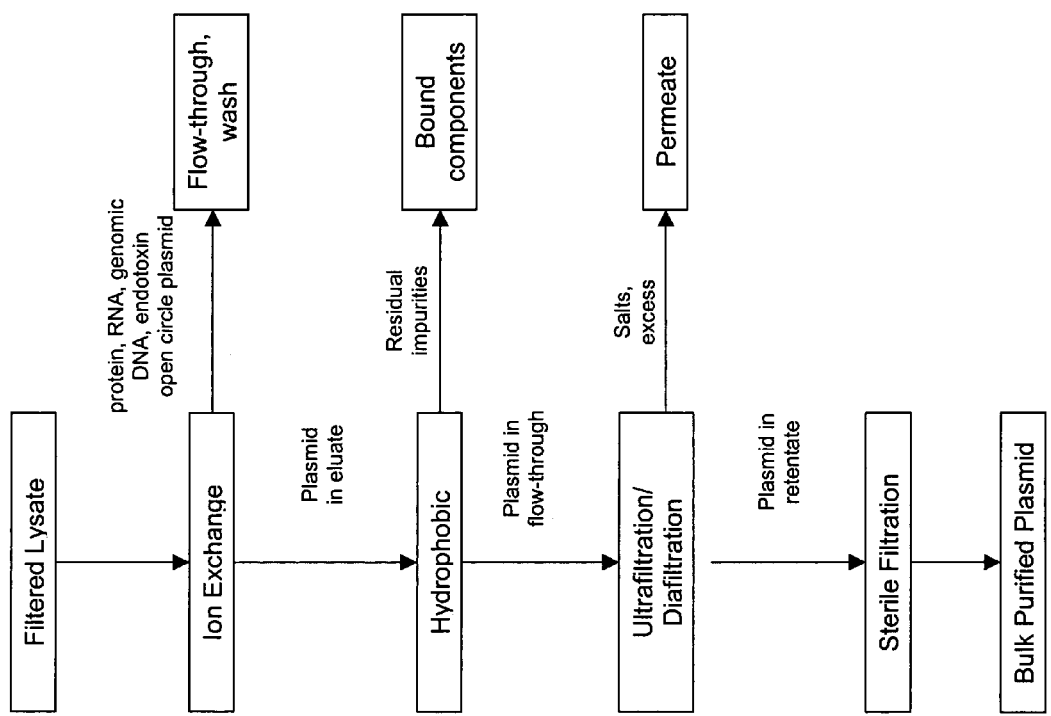
FIG. 5 is a flowchart of product purification, concentration/desalting, and sterile filtration.

FIG. 5 depicts a flowchart of the product purification process, beginning with clarified or filtered lysate and ending with bulk purified product. Advantageously, the process is based entirely on membrane separation steps, and avoids any column chromatography. As a result, the process has high capacity, high fluid flow rates, is inexpensive, scalable, and can be performed easily and rapidly. The product to be purified may be any cellular component of interest. Preferably, it is a macromolecule such as a protein or a plasmid. More preferably it is a plasmid. The lysate used as a starting material for the purification process may be produced by any suitable means. Preferably, the lysate is prepared according to the methods and apparatus provided in the present invention. However, one skilled in the art will be aware of many other methods to produce cell lysates, and will be able to apply the present purification process to such lysates using no more than ordinary experimentation.

In the first purification step, the lysate is applied to an ion exchange membrane. The cellular component of interest may bind to the membrane, while impurities flow through or are washed off of the membrane to separate them from the product of interest. Alternatively, the product may flow through the membrane, while impurities are retained. In a preferred embodiment, the product binds to the membrane. In such a case, it is preferable to ensure that the ionic strength of the lysate is low enough to provide substantially complete binding of the cellular component of interest to the ion exchange membrane. If necessary, this can be accomplished by diluting a high ionic strength lysate with a sufficient quantity of water or other low ionic strength solution. After washing to remove weakly bound impurities, the product is eluted from the membrane. Preferably, the elution is accomplished by flowing a salt solution through the membrane. The salt solution has a strength, concentration, or conductivity sufficient to overcome the binding of the product to the membrane. The product is thus recovered in the eluate.

In the second purification step, the partially purified product recovered from the ion exchange membrane is optionally subjected to a hydrophobic interaction membrane. The product may bind to the membrane, while impurities flow through or are washed off, or the product may flow through while impurities bind. In a preferred embodiment, the product flows through. The eluate from the ion exchange membrane may be conditioned prior to flowing onto the hydrophobic interaction membrane. Typically, such conditioning involves adding a desired amount of a desired salt. Ammonium sulfate is preferred, in an amount suitable to provide binding of the product or the impurities, as desired. This step may be omitted from the process for certain applications.

Purified product recovered from the hydrophobic interaction membrane is then subjected to ultrafiltration/diafiltration to concentrate the product, remove excess salts, and if desired, change the composition of the diluent. Methods for performing ultrafiltration/diafiltration are well known to those of skill in the art, and have been employed for biologically active molecules such as proteins and plasmids for many years. Tangential flow filtration is preferred, but batch methods are also known. Any such method that meets the practitioner's need may be employed.

Concentrated desalted product recovered in the retentate from the ultrafiltration/diafiltration is optionally subjected to sterile filtration, if a sterile product is desired. Methods for sterile filtration are well known to those of skill in the art, and any such method may be selected. The resulting material comprises a substantially purified cellular component of interest. The product may be used for a variety of purposes, including, but not limited to, pharmaceutical, veterinary, or agricultural applications.

One skilled in the art will recognize that the purification process provided herein may be applied to a wide variety of cellular components of interest, while still retaining the described benefits. Details of the process, including the preferred nature of the membranes used, and the preferred conditions for using them, will depend on the nature of the product of interest. Preferably, the product is a plasmid, and the lysate is prepared from plasmid-containing cells. More preferably, the plasmid-containing cells are lysed with alkali, detergent, or a combination thereof, and the alkaline lysate is subsequently neutralized and precipitated with potassium acetate, ammonium acetate, acetic acid, or a combination thereof. Most preferably, the lysate is prepared by the methods and apparatus provided in the present invention. Although any ion exchange membrane may be suitable, preferably it is an anion exchange membrane. More preferably, it is a strong anion exchange membrane, comprising quaternary amine groups. Examples of such membranes include, but may not be limited to the Mustang™ Q (Pall Corp., East Hills, N.Y.), Sartobind® Q (Sartorius, Goettingen, Germany), and Intercept™ Q (Millipore, Billerica, Mass.). Similarly, the hydrophobic interaction membrane may be any such membrane that binds either cellular components of interest or impurities based primarily on hydrophobic interactions. The following discussion provides a detailed description of the preferred embodiments when purifying a plasmid from a lysate prepared by the methods and apparatus provided herein. This description is in no way intended to limit the scope of the present invention, as one skilled in the art will be able to adjust the described purification process to accommodate any suitable cellular component of interest, using no more than ordinary experimentation. Such adjustments may include, but are not limited to, selecting different membranes; selecting different solution conditions for conditioning, loading, washing, or eluting membranes; selecting different flow rates; etc. Details of such selections will be primarily dictated by the nature and properties of the cellular component of interest. All such embodiments are intended to be encompassed by the present invention.

Preferably, where plasmid-containing cells are lysed according to the methods and apparatus provided herein, the ion exchange membrane purification step comprises purification using a Pall Mustang™ Q cartridge. Preferably, the clarified, filtered lysate is adjusted to a conductivity of less than about 85 mS/cm by dilution with a suitable amount of purified water. More preferably, the conductivity is adjusted to about 80–85 mS/cm. Preferably, an amount of purified water equal to about 1.5-times the lysate volume is used for dilution. The Mustang™ Q cartridge is conditioned by flowing a suitable Q equilibration/wash solution through it. Preferably, the Q equilibration/wash solution comprises about 0.67 M NaCl. All solutions may also include a buffering agent, a chelating agent, or a combination thereof. Preferably, these solutions contain about 10 mM Tris and about 1 mM $Na_2EDTA$, with a pH of about 8. Preferably, Q equilibration/wash solution is pumped through the cartridge at about 180–350 bed volumes per hour (BV/hr). Diluted lysate is then pumped onto the cartridge, preferably at less than about 1,200 BV/hr, more preferably at about 450–700 BV/hr. The loaded cartridge is then washed with Q equilibration/wash buffer, preferably at a flow rate of about 180–350 BV/hr. Washing is preferably continued until the absorbance at 260 nm ($A_{260}$) of the effluent returns to approximately baseline. Plasmid is eluted with a solution that preferably comprises about 1 M NaCl, about 10 mM Tris, about 1 mM $Na_2EDTA$, and about pH 8. Elution is preferably performed at a flow rate of 140–350 BV/hr, more preferably at 160–210 BV/hr. Preferably, elution is continued until the $A_{260}$ of the eluate returns to about baseline. Alternately, an empirically determined elution volume may be applied. The eluate is collected for subsequent purification using hydrophobic interaction.

Optionally, when purifying plasmid according to the present invention, the eluate from the Pall Mustang™ Q cartridge is next subjected to further purification using a hydrophobic interaction membrane. Preferably, the membrane is any of a class of "hydrophilic" cartridges (HIC). The cartridge is preferably conditioned by flowing a HIC equilibration/wash solution comprising concentrated ammonium sulfate through it. Preferably, the HIC equilibration/wash solution comprises about 2.4 M ammonium sulfate, about 10 mM Tris, about 1 mM $Na_2EDTA$, and about pH 8. Preferably, the conductivity of the HIC equilibration/wash solution is about 240–260 mS/cm, more preferably about 245–255 mS/cm.

The eluate from the ion exchange membrane is preferably conditioned by diluting it with about 2 volumes of a solution comprising about 4.1 M ammonium sulfate. The conductivity of the resulting diluted eluate is preferably about 240–260 mS/cm, more preferably about 245–255 mS/cm. The diluted eluate is flowed through the conditioned HIC cartridge, preferably at a flow rate of about 100–200 BV/hr. The flow-through is collected for subsequent ultrafiltration/diafiltration. Optionally, the HIC cartridge may be washed with water, and the wash solution recovered to analyze the impurities removed from the product.

Purified product recovered from the hydrophobic interaction membrane is concentrated and desalted by ultrafiltration/diafiltration. It will be well within the ability of one skilled in the art to perform ultrafiltration/diafiltration using known methods. Ultrafiltration/diafiltration membranes may be selected based on nominal molecular weight cut-off ("NMWCO") so as to retain the product of interest in the retentate, while allowing low molecular weight materials such as salts to pass into the filtrate. One skilled in the art will be able to select such membranes based on the size and nature of the product of interest, coupled with no more than ordinary experimentation. In a preferred embodiment, where the product is a plasmid about 1–8 kb in size, ultrafiltration/diafiltration is performed using a Pall Centramate™ unit, and the membranes used are Pall Omega™ suspended screen membrane cassettes with a NMWCO of 100 kD. Preferably, the plasmid is concentrated to at least about 2.5 mg/mL. Any buffering solution or sterile water may be used during the final buffer exchange step, and will affect the final pH and conductivity of the product.

Concentrated, desalted product may, if desired, be further subjected to sterile filtration. Various methods for performing such an operation are well known, and will be within the capability of those skilled in the art. Where the product is a plasmid, sterile filtration may preferably be performed using a Pall AcroPak™ 200 filter with a 0.22 μm cut-off. The resulting purified, concentrated, desalted, sterile-filtered plasmid is substantially free of impurities such as protein, genomic DNA, RNA, and endotoxin. Residual protein, as determined by bicinchoninic acid assay (Pierce Biotechnology, Rockford, Ill.) will preferably be less than about 1% (by weight), and more preferably less than or equal to about 0.1%. Residual endotoxin, as determined by *limulus amebocyte* lysate ("LAL") assay, will preferably be less than about 100 endotoxin units per milligram of plasmid (EU/mg). More preferably, endotoxin will be less than about 50 EU/mg, most preferably less than about 20 EU/mg. Residual RNA is preferably less than or about 5% by weight, more preferably less than or about 1% (by agarose gel electrophoresis or hydrophobic interaction HPLC). Residual genomic DNA is preferably less than about 5% by weight, more preferably less than about 1% (by agarose gel electrophoresis or slot blot).

In one embodiment, the present invention comprises all of the methods and apparatus described herein, as outlined in FIG. 1. One skilled in the art will recognize that the present invention may be modified by adding, subtracting, or substituting selected steps or methods. All such modifications are contemplated to be part of the present invention. Thus, in one embodiment, the present invention provides for methods of lysing cells by mixing a cell suspension with a lysis solution using a high shear, low residence-time mixing device. In another embodiment, the invention provides for methods of mixing a cell suspension, a cell lysate, or a fluid containing cellular components of interest with one or more additional fluids using a bubble mixer. In a further embodiment, the invention provides for mixing a cell lysate with a precipitating solution using a bubble mixer, while simultaneously entrapping gas bubbles in the precipitated cellular components. In yet another embodiment, the present invention provides for a device comprising a bubble mixer that may be used to practice the above methods. Still further, the present invention provides for methods of lysing cells, comprising a combination of mixing a cell suspension with a lysis solution using a high shear, low residence-time mixer, followed by mixing the lysed cells with a precipitating solution using a bubble mixer. In another embodiment, the invention provides for a method to separate precipitated cellular components from a fluid lysate, comprising entrapping gas bubbles in the precipitated cellular components using a bubble mixer, collecting the materials in a tank, allowing the precipitated cellular components to form a floating layer, optionally applying a vacuum to compact the precipitated components and degas the lysate, and recovering the fluid lysate by draining or pumping it out from underneath the precipitated components. In yet another embodiment, the present invention provides a method for purifying cellular components of interest from a cell lysate, comprising subjecting the lysate to an ion exchange membrane, optionally a hydrophobic interaction membrane, an ultrafiltration/diafiltration procedure, and optionally, a sterile filtration procedure. Each of the current embodiments, as well as any combination of one or more embodiments, is further encompassed by the present invention.

The innovative teachings of the present invention are described with particular reference to the steps disclosed herein with respect to the production of plasmids. However, it should be understood and appreciated by those skilled in the art that the use of these steps and processes with respect to the production of plasmids provides only one example of the many advantageous uses and innovative teachings herein. Various non-substantive alterations, modifications and substitutions can be made to the disclosed process without departing in any way from the spirit and scope of the invention. The following examples are provided to illustrate the methods and devices disclosed herein, and should in no way be construed as limiting the scope of the present invention.

EXAMPLE 1

E. coli cells containing plasmid pAV0124 were fermented to high density and recovered by centrifugation. Approximately 4.0 kg (wet weight) of cell paste was suspended in a resuspension buffer comprising 25 mM Tris, 10 mM Na$_2$EDTA, pH 8, to a final volume of approximately 28 L. The resulting cell suspension had an OD$_{600}$ of 65.8. This cell suspension was pumped at 300 mL/min into one side of a "Y" connector. Simultaneously, lysis solution comprising 0.2 N NaOH and 1% SDS was pumped at 300 mL/min into the other side of the "Y" connector. The combined fluids exiting the "Y" connector were immediately passed through a Silverson Model L4R rotor/stator mixer fitted with a standard Emulsor Screen and an In-line assembly. The mixer was operated at a rotor speed of 765 rpm.

The fluid exiting the rotor/stator mixer was passed through a 50-foot, 0.625 inch ID holding coil. At a total flow rate of approximately 600 mL/min, transit time through the holding coil was approximately 5 minutes, which allowed for complete cell lysis.

Cell lysate exiting the holding coil entered a bubble mixer as shown in FIG. 3. Simultaneously, cold (approximately 4° C.) neutralization/precipitation solution comprising 1 M potassium acetate and 7 M ammonium acetate was independently pumped into the bubble mixer at 600 mL/min. The lysate and neutralization/precipitation solutions were flowed vertically up the mixing column and through the outlet near the top. While the solutions passed through the mixing column, compressed air was introduced into the bottom of the column at a rate of approximately 2 slpm through a sintered sparger designed to provide a constant stream of fine bubbles. Untrapped air was vented through the top of the column. As the cell lysate and neutralization/precipitation solutions passed through the column, they were continuously mixed by the turbulence of the rising bubbles. This was evidenced by the formation of a white, flocculent precipitate comprising potassium SDS, denatured cellular proteins, bound lipids and cell wall components, and associated genomic DNA. The neutralized precipitated lysate exiting the bubble mixer was collected in a settling container.

This process was operated in a continuous mode until the entire cell suspension had been lysed, neutralized and precipitated, and collected in the settling tank. Total solution volumes included 28 L of cell suspension, a 5 L wash of the resuspension tank with resuspension buffer, 33 L of lysis solution, and 56 L of neutralization/precipitation solution, for a total volume of approximately 122 L.

After collection, the material in the settling tank was observed through a sight glass in the side of the settling tank. The flocculent precipitate could be seen rising to the surface of the liquid, aided by clearly visible air bubbles that were entrapped in the solids. A vacuum of approximately 28 in. (Hg) was applied to the settling tank, leading to some compaction of the floating precipitate and degassing of the fluid lysate.

The material was held under vacuum in the settling tank at room temperature for approximately 17 hours. The vacuum was then slowly vented to avoid disrupting the compacted precipitate. The plasmid-containing clarified lysate was carefully pumped from the tank through a sanitary fitting at the bottom. The liquid and precipitate levels in the tank were visually monitored through the sight glass, and pumping was halted in time to ensure that the precipitate did not exit the tank. Approximately 106 L of clarified lysate was recovered. This was subjected to 5 µm filtration, followed by 0.2 µm final filtration. A portion of the lysate was lost during filtration, due to clogging of the filters. As a result, approximately 80 L of filtered lysate was obtained. A small sample of this material was taken for plasmid concentration analysis, and the remainder of the filtered lysate was then diluted with approximately 140 L of purified water, in preparation for further purification. Plasmid concentration in the filtered lysate (prior to dilution) was estimated by anion exchange HPLC to be approximately 41 µg/mL, corresponding to approximately 3300 mg of total plasmid.

EXAMPLE 2

The filtered, diluted lysate from Example 1 was further purified by anion exchange. A 260 mL bed volume Pall Mustang™ Q cartridge was equilibrated with 4 L of Q equilibration/wash solution, comprising 10 mM Tris, 1 mM Na$_2$EDTA, 0.67 M NaCl, pH 8. 220 L of material prepared in Example 1 was pumped onto the Q cartridge at a flow rate of approximately 2–3 L/min. After loading, the cartridge was washed with equilibration buffer at approximately 1 L/min until the A$_{260}$ of the effluent approached baseline. Plasmid was eluted from the cartridge with Q elution buffer, comprising 10 mM Tris, 1 mM Na$_2$EDTA, 1 M NaCl, pH 8, pumped at 800 mL/min. Absorbance of the cartridge effluent at 260 nm was monitored and recorded using a strip-chart recorder. Elution was terminated when the A$_{260}$ returned to baseline. Total eluate volume was approximately 7.0 L and contained a total of approximately 3900 mg of DNA based on A$_{260}$ (assuming a 1 mg/mL solution of DNA has an A$_{260}$ of 1.0 in a 1 cm path length cell).

The Q eluate was further purified by hydrophobic interaction. The conductivity of the eluate was brought to approximately 250 mS/cm by adding 13.9 L of 4.1 M ammonium sulfate. A 60 mL bed volume HIC cartridge was equilibrated with approximately 1.3 L of 2.4 M ammonium sulfate, pumped at 400 mL/min. The conditioned Q eluate was then pumped through the HIC cartridge at approximately 200 mL/min. The flow-through contained approximately 3800 mg of DNA by A$_{260}$.

A portion of the HIC flow-through material, corresponding to approximately 2700 mg of DNA, was concentrated and desalted by ultrafiltration/diafiltration ("UF/DF"), using a Pall Centramate™ cassette holder fitted with four Pall Omega™ suspended screen membrane cassettes, with an area of 1 ft$^2$ per cassette and a nominal molecular weight cut-off of 100 kD. 826 mL of bulk retentate was recovered, with a DNA concentration of 2.6 mg/mL (by A$_{260}$). The UF/DF apparatus was washed once with water for injection ("WFI"), yielding 291 mL at a concentration of 1.6 mg/mL. Combined DNA recovery after UF/DF was approximately 2600 mg.

A portion of the UF/DF material, corresponding to approximately 2300 mg of DNA, was subjected to sterile filtration bypassing through a Pall AcroPak™ 200, 0.22 µm filter. A total of 893 mL of final product was recovered, at a DNA concentration of 2.5 mg/mL, corresponding to a total of 2200 mg.

The final product was subjected to a battery of tests for purity and quality. Residual protein levels were ≦0.1% by bicinchoninic acid ("BCA") assay. Residual RNA was ≦0.3% by hydrophobic interaction HPLC. Residual genomic DNA was approximately 0.2% by agarose gel electrophoresis. Endotoxin levels were 5 EU/mg by *limulus amebocyte* lysate. These values compare favorably with those provided by previously disclosed methods, and indicate that plasmids prepared by the methods disclosed herein are suitable for a variety of uses, including, but not limited to, human or veterinary gene therapy, non-viral plasmid-mediated therapy, and DNA vaccine applications.

EXAMPLE 3

E. *coli* cells containing plasmid pAV0124 were fermented to high density and recovered by centrifugation. Approximately 3.8 kg (wet weight) of cell paste was suspended in 31.6 L of resuspension buffer, to an $OD_{600}$ of 79.4. Lysis, neutralization/precipitation, and collection in the settling tank were performed as in Example 1. Flow rates were 300 mL/min for cell suspension and lysis solution, and 600 mL/min for neutralization/precipitation solution. The Silverson L4R, fitted as before, was operated at a rotor speed of 747 rpm. Transit time through the holding coil between lysis and neutralization/precipitation was approximately 5 minutes. Compressed air was sparged through the bubble mixer at 2 slpm. Total fluid volumes included 26.6 L of cell suspension, 5 L of resuspension tank wash with resuspension buffer, 31.6 L of lysis solution, and 53.2 L of neutralization/precipitation solution, for a nominal total of 116.4 L.

Once all of the material was collected in the settling tank, a vacuum of 26 in. Hg was applied, and the tank was chilled and held for approximately 18.3 hours at 2–8° C. Crude lysate was recovered and filtered as before, yielding 85 L of clarified lysate. A small sample of the filtered lysate was taken for plasmid concentration analysis (see below), and the remainder was diluted with 135 L of purified water, yielding a total of 220 L of cleared, filtered, diluted lysate.

HPLC analysis indicated the plasmid concentration in the undiluted filtered lysate was approximately 37 μg/mL, corresponding to approximately 3100 mg of total plasmid. For comparison, a small sample of the same cell paste was lysed at bench scale, using the same resuspension, lysis, and neutralization/precipitation solutions in proportions comparable to the large scale lysis. Gentle hand mixing was used at all steps. The plasmid concentration in the hand mixed lysate was estimated to be 42 μg/mL, comparable to the concentration in the large scale lysate. This demonstrates that the large scale lysis procedure is effective in releasing plasmid from the cells. Furthermore, the comparability of these results with those obtained in Example 1 demonstrates the reproducibility and robustness of the disclosed inventions.

EXAMPLE 4

The clarified, filtered, diluted lysate from Example 3 was further purified by Pall Mustang™ Q anion exchange membrane chromatography. After sanitization and regeneration, a 260 mL bed volume cartridge was equilibrated with 4 L of Q equilibration/wash solution, as in Example 2. 220 L of material prepared in Example 3 was pumped onto the Q cartridge at a flow rate of 2 L/min. The cartridge was washed with 4 L of Q equilibration/wash solution at 1.2 L/min. Plasmid was then eluted from the cartridge with Q elution solution, pumped at 600 mL/min. Eluate absorbance at 260 nm was monitored and recorded using a strip-chart recorder, and elution was terminated when $A_{260}$ returned to baseline. Total eluate volume was 4.0 L, with a DNA concentration of 0.89 mg/mL (by $A_{260}$). Total DNA recovered was approximately 3600 mg.

The Q eluate was concentrated and desalted by ultrafiltration/diafiltration, using a Pall Centramate™ cassette holder fitted with four Pall Omega™ suspended screen membrane cassettes, with an area of 1 ft² per cassette and a nominal molecular weight cut-off of 100 kD. 679.3 mL of bulk retentate was recovered, with a DNA concentration of 4.1 mg/mL (by $A_{260}$). The UF/DF rig was washed twice with WFI. Wash 1 yielded 187.8 mL with a concentration of 1.7 mg/mL. Wash 2 yielded 257.7 mL with a concentration of 0.55 mg/mL. Bulk retentate was combined with all of washes 1 and 2, plus an additional 179.9 mL of WFI. This resulted in 1275.5 mL of final product at a concentration of 2.5 mg/mL, for a final recovery of 3200 mg of plasmid.

Purity analysis of the final product indicated that residual protein was ≦0.1%, and residual genomic DNA was approximately 0.1%, comparable to what was observed in Example 2. RNA and endotoxin levels were higher than in the previous example, at 6% and 142 EU/mg, respectively. These results demonstrate that the HIC step may be omitted if higher levels of RNA and endotoxin impurities are acceptable. They further demonstrate that the HIC step is particularly effective in removing residual RNA and endotoxin for critical applications.

EXAMPLE 5

Samples from the above listed examples were subjected to analysis by agarose gel electrophoresis to further confirm the quality of the product and relative quantity of impurities. The agarose gel was significantly overloaded with plasmid. The gel was designed to detect trace amounts of nucleic acid impurities in the plasmid bulk product. The locations of contaminating genomic DNA and RNA were noted as very faint bands in the final product samples. The percentage of impurities visualized on this gel was consistent with the quantified values provided by other methods.

A constant mass gel was also loaded with reasonably consistent amounts of supercoiled plasmid in each lane. The gel compared the current lysis technique to the classic hand lysis method, both in terms of the quantity and quality of product extracted. Further lanes showed the removal of impurities at different steps of the process, as well as an enrichment of the supercoiled form. A sample prepared by vigorous hand lysis showed large amounts of contaminating genomic DNA and RNA. The amount of impurities in the samples containing filtered lysate was comparable to that in the samples containing plasmid prepared by gentle hand lysis. Samples containing plasmid that was further subjected to ion exchange chromatography showed even less impurities, as did the samples containing the bulk drug substance. Both batches verify the consistency of the process.

The embodiments provided herein illustrate an apparatus and methods for isolating plasmid DNA from cells. One skilled in the art readily appreciates that this invention is well adapted to carry out the objectives and obtain the ends and advantages mentioned as well as those inherent therein. The entire apparatus, bubble mixer-chamber, methods, procedures, and techniques described herein are presently representative of the preferred embodiments and are intended to be exemplary and are not intended as limitations of the scope. Changes therein and other uses will occur to those skilled in the art which are encompassed within the spirit of the invention or defined by the scope of the claims.

REFERENCES CITED

The following U.S. Patent documents and publications are incorporated by reference herein.

U.S. Patent Documents

U.S. Pat. No. 5,438,128 Method for Rapid Purification of Nucleic Acids Using Layered Ion-Exchange Membranes, Nieuwkerk U.S. Pat. No. 5,482,836 DNA Purification by Triplex-Affinity Capture and Affinity Capture Electrophoresis, Cantor
U.S. Pat. No. 5,561,064 Production of Pharmaceutical-Grade Plasmid DNA, Marquet
U.S. Pat. No. 5,591,841 Rapid Purification of Circular DNA by Triplex-Mediated Affinity Capture, Ji
U.S. Pat. No. 5,625,053 Method of Isolating Purified Plasmid DNA Using a Nonionic Detergent Solution, Kresheck
U.S. Pat. No. 5,650,506 Modified Glass Fiber Membranes Useful for DNA Purification by Solid Phase Extraction, Woodard
U.S. Pat. No. 5,665,554 Magnetic Bead Precipitation Method, Reeve
U.S. Pat. No. 5,693,785 Purification of DNA on Hydroxylated Silicas, Woodard
U.S. Pat. No. 5,707,812 Purification of Plasmid DNA During Column Chromatography, Horn
U.S. Pat. No. 5,808,041 Nucleic Acid Purification Using Silica Gel and Glass Particles, Padhye
U.S. Pat. No. 5,837,529 Method for Lysing Cells, Wan
U.S. Pat. No. 5,843,731 Method for Purifying Plasmid DNA on Calcium Phosphate Compound, Yamamoto
U.S. Pat. No. 5,898,071 DNA Purification and Isolation Using Magnetic Particles, Hawkins
U.S. Pat. No. 5,981,735 Method of Plasmid DNA Production and Purification, Thatcher
U.S. Pat. No. 5,986,085 Matched Ion Polynucleotide Chromatography (MIPC) Process for Separation of Polynucleotide Fragments, Gjerde
U.S. Pat. No. 5,990,301 Process for the Separation and Purification of Nucleic Acids from Biological Sources, Colpan
U.S. Pat. No. 6,011,148 Methods for Purifying Nucleic Acids, Bussey
U.S. Pat. No. 6,197,553 Method for Large Scale Plasmid Purification, Lee
U.S. Pat. No. 6,235,892 Process for the Purification of Nucleic Acids, Demmer
U.S. Pat. No. 6,395,516 Vessel for Mixing a Cell Lysate, Nienow
U.S. Pat. No. 6,410,274 Plasmid DNA Purification Using Divalent Alkaline Earth Metal Ions and Two Anion Exchangers, Bhikhabhai
US 2001/0034435 Process and Equipment for Plasmid Purification, Nochumson
US 2002/0198372 Methods for Purifying Nucleic Acids, Bridenbaugh Foreign Patent Documents
WO 97/35002 Purification of Pharmaceutical-Grade Plasmid DNA, Wils
WO 98/30685 Purification and/or Concentration of DNA by Cross-Flow Filtration, Separation of Endotoxins from a Nucleic Acid Preparation, Kuhne
WO 00/05358 Methods for Purifying Nucleic Acids, Bridenbaugh
WO 01/94573 Processing of Plasmid-Containing Fluids, Yang
WO 04/024283 Apparatus and Method for preparative scale purification of nucleic acids, AU-Yeung,

OTHER REFERENCES

Birnboim and Doly, 1979, *Nucleic Acids Res.* 7, 1513–1523.
Carlson et al., 1995, *Biotechnol. Bioeng.* 48, 303–315.
Levy et al., 2000, *Trends Biotechnol.* 18, 296–305.
Marquet et al., 1995, *Biopharm* 8, 26–37.
Rathore et al., 2003, *Biopharm International, March,* 30–40.
Sambrook et al., *Molecular Cloning: A Laboratory Manual,* $2^{nd}$ Ed., Cold Spring Harbor Laboratory Press, Cold Spring Harbor, N.Y.
Varley et al., 1999, *Bioseparation* 8, 209–217.

What is claimed is:

1. An apparatus for isolating cellular component of interest from cells comprising:
   (a) a first tank, wherein the first tank is used for holding a suspension of cells having the cellular component of interest;
   (b) a mixer in fluid communication with the first tank;
   (c) a second tank in fluid communication with the mixer, wherein the second tank is used for holding a lysis solution;
   (d) a holding coil in fluid communication with the mixer; and
   (e) a bubble-mixer chamber with a top and a bottom having:
      (i) a first inlet in fluid communication with the holding coil;
      (ii) a second inlet in fluid communication with a third tank, wherein the third tank is used for holding a precipitation solution, a neutralization solution, or a mixture thereof;
      (iii) a third inlet in fluid communication with a gas source;
      (iv) a vent; and
      (v) an outlet in fluid communication with a fourth tank, wherein the fourth tank is used for separating precipitated cellular components from fluid cell lysate;
   wherein,
   the mixer is a high-shear, low-residence-time-mixing-device, wherein the residence-time is less than or equal to about one second; the suspension of cells having the plasmid DNA from the first tank is allowed to flow into the mixer; the lysis solution from the second tank is allowed to flow into the mixer; a lysate-mixture is allowed to flow from the mixer into the holding coil; the lysate-mixture from the holding coil is allowed to flow into the bubble-mixer chamber; the precipitation solution, the neutralization solution, or the mixture thereof from the third tank is allowed to flow into the bubble-mixer chamber; and a suspension containing the cellular component of interest is allowed to flow from the bubble-mixer chamber into the fourth tank.

2. The apparatus of claim 1, further comprising: a first pump for transporting the suspension of cells having the cellular component of interest from the first tank into the mixer; a second pump for transporting the lysis solution from the second tank into the mixer; a third pump for transporting the precipitation solution, the neutralization solution, or the mixture thereof, from the third tank into the bubble-mixer chamber.

3. The apparatus of claim 2, wherein the first pump and the second pump are combined in a dual head pump allowing the suspension of cells having the cellular component of interest and the lysis solution to be simultaneously pumped to the mixer having a linear flow rate of about 0.1–1 ft/second.

4. The apparatus of claim 2, further comprising: a Y-connector having a first bifurcated branch, a second bifurcated branch and an exit branch, wherein the first tank is in fluid communication with the first bifurcated branch of the Y-connector through the first pump; the second tank is in fluid communication with the second bifurcated branch of the Y-connector through the second pump; and the mixer is in fluid communication with the exit branch of the Y-connector, wherein the first and second pumps provide a linear flow rate of about 0.2 to 2 ft/second for a contacted fluid exiting the Y-connector.

5. The apparatus of claim 2, further comprising:
a fourth pump in fluid communication with the fourth tank;
a first filter in fluid communication with the fourth pump;
a second filter in fluid communication with the first filter; and
a fifth tank for holding a clarified lysate.

6. The apparatus of claim 5, wherein the first filter has a particle size limit of about 5–10 μm and the second filter has a cut of about 0.2 μm.

7. The apparatus of claim 1, wherein gravity, pressure, vacuum, or a mixture thereof, is used for:
transporting the suspension of cells having the cellular component of interest from the first tank into the mixer;
transporting the lysis solution from the second tank into the mixer; and
transporting the precipitation solution, the neutralization solution, or the mixture thereof, from the third tank into the bubble-mixer chamber.

8. The apparatus of claim 1, wherein the bubble-mixer chamber comprises:
a closed vertical column with the vent at the top of the column;
the first inlet entering the bubble-mixer chamber being proximal to the bottom of a first side of the closed vertical column;
the second inlet entering the bubble-mixer chamber being proximal to the bottom on a second side and opposite of the first inlet;
the third inlet entering the bubble-mixer chamber being proximal to the bottom and about in the middle of the first and second inlets; and
the outlet exiting the bubble mixing chamber being proximal to the top of the closed vertical column.

9. The apparatus of claim 8, wherein the third inlet further comprises a sintered sparger inside the closed vertical column.

10. The apparatus of claim 1, wherein the mixer comprises a device that mixes in a flow through mode having a rotor/stator mixer or emulsifier and linear flow rates from about 0.1 L/min to about 20 L/min.

11. The apparatus of claim 1, wherein, at a fixed linear flow rate, the holding coil comprises tubing having a length and a diameter sufficient to allow the lysate-mixture leaving the mixer about 2 to about 8 minutes contact time with the holding coil before the lysate-mixture can enters the bubble-mixer chamber.

12. The apparatus of claim 1, wherein the fourth tank further comprises an impeller mixer sufficient to provide uniform mixing of fluid without disturbing a flocculent precipitate.

13. The apparatus of claim 1, further comprising a vacuum pump in communication with the fourth tank.

14. The apparatus of claim 1, wherein the cellular component of interest comprises a plasmid DNA.

* * * * *